(12) United States Patent
Sehgal et al.

(10) Patent No.: US 7,179,459 B2
(45) Date of Patent: Feb. 20, 2007

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Glenview, IL (US); Jonathan Wong, Chicago, IL (US)

(73) Assignee: Biovec, LLC, Chicago, IL (US)

( * ) Notice: Subject to any disclaimer, the term of this patent is extended or adjusted under 35 U.S.C. 154(b) by 190 days.

(21) Appl. No.: 10/725,013

(22) Filed: Dec. 2, 2003

(65) Prior Publication Data

US 2004/0198683 A1    Oct. 7, 2004

Related U.S. Application Data

(60) Provisional application No. 60/430,099, filed on Dec. 2, 2002.

(51) Int. Cl.
| | |
|---|---|
| A01N 63/00 | (2006.01) |
| A61K 48/00 | (2006.01) |
| C12N 5/00 | (2006.01) |
| C12N 5/02 | (2006.01) |
| C12N 15/86 | (2006.01) |
| C12N 5/08 | (2006.01) |

(52) U.S. Cl. .................. 424/93.21; 435/325; 435/456; 435/372

(58) Field of Classification Search ............... 424/93.2, 424/93.21; 435/325, 456, 372
See application file for complete search history.

(56) References Cited

U.S. PATENT DOCUMENTS

| | | | | |
|---|---|---|---|---|
| 4,826,811 A | * | 5/1989 | Sehgal et al. .................. 514/6 |
| 5,981,225 A | * | 11/1999 | Kochanek et al. ......... 435/69.1 |
| 6,290,949 B1 | * | 9/2001 | French et al. ............... 424/93.2 |

OTHER PUBLICATIONS

Kibbe et al. (J. Vasc. Surg. 34: 156-65, 2001).*
He et al. (PNAS, 95: 2509-2514).*
Brian S. Zuckerbraun et al., "Vascular Gene Therapy, A Reality of the 21st Century," Arch. Surg. 137:854-61 (2002).
Melina R. Kibbe et al., "Gene Therapy for Restenosis," Circ. Res. 86:829-33 (2000).
Larry L. Shears et al., "Efficient Inhibition of Intimal Hyperplasia by Adenovirus-Mediated Inducible Nitric Oxide Synthase Gene Transfer to Rats and Pigs In Vivo," J. Am. Coll. Surg., 187(3):295-306 (1998).
Russell Ross, "The pathogenesis of atherosclerosis: a perspective for the 1990s," Nature, 362:801-9 (1993).
J. Evan Sadler, "Thrombomodulin Structure and Function," Tehomb Haemost., 78:392-5 (1997).
Charles T. Esmon, "Thrombomodulin as a model of molecular mechanisms that modulate protease specificity and function at the vessel surface," Faseb J., 9:946-55 (1995).
Veikko Salomaa et al., "Soluble thrombomodulin as a predicctor of incident coronary heart disease and symptomless carotid artery atherosclerosis in the Atherosclerosis Risk in Communities (ARIC) Study: a case-cohort study," Lancet, 353:1729-34 (1999).
R.M.J. Palmer et al., "Nitric oxide release accounts for the biological activity of endothelium-derived relaxing factor," Nature, 327:524-6 (1987).
P. Kubes et al., "Nitric oxide: An endogenous modulator of leukocyte adhesion," Proc. Natl. Acad. Sci. USA, 88:4651-5 (1991).
P. Gabriel Steg M.D., et al., "Reduction of Restenosis After Angioplasty in an Atheromatous Rabbit Model by Suicide Gene Therapy," Circulation, 96:401-11 (1997).
Eric Van Belle et al., "Accelerated Endothelialization by Local Delivery of Recombinant Human Vascular Endothelial Growth Factor Reduces In-Stent Intimal Formation," Biochem. and Biophs. Res. Communications, 235 311-6 (1997).
A. Neil Salyapongse, M.D., et al., "Gene Therapy and Tissue Engineering," Tissue Engineering, 26(4):663-76 (1999).
T. Kon et al., "Bone Morphogenetic Protein-2-Stimulates Differentiation of Cultured Spinal Ligament Cells from Patients with Ossification of the Posterior Longitudinal Ligament," Calcif. Tissue Int. (1997) 60:291-6.

* cited by examiner

*Primary Examiner*—Brian Whiteman
(74) *Attorney, Agent, or Firm*—DLA Piper US LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel ex vitro using a gutless adenovirus vector. Another aspect of the present invention is to provide a method to deliver a gutless adenovirus vector carrying a DNA sequence encoding a TM protein or its variant using a stent.

14 Claims, 14 Drawing Sheets

Left Inverted Terminal Repeat: 1-103

Encapsidation Signal (Ψ): 183-331

HPRT Introns: 365-10557

Right Inverted Terminal Repeat: 10571-10673 pBR322 ori: 10877-11544

Kanamycin Resistance Gene: 12353-13144

SEQ ID NO:1 pSHuttle Sequence

CATCATCAATAATATACCTTATTTTGGATTGAAGCCAATATGATAATGAGGGGGTGGAGTTTGTGACG
TGGCGCGGGGCGTGGGAACGGGGCGGGTGACGTAGTAGTGTGGCGGAAGTGTGATGTTGCAAGTGTG
GCGGAACACATGTAAGCGACGGATGTGGCAAAAGTGACGTTTTTGGTGTGCGCCGGTGTACACAGGA
AGTGACAATTTTCGCGCGGTTTTAGGCGGATGTTGTAGTAAATTTGGGCGTAACCGAGTAAGATTTGG
CCATTTTCGCGGGAAAACTGAATAAGAGGAAGTGAAATCTGAATAATTTTGTGTTACTCATAGCGCGT
AATACTGGTACCGCGGCCGCCTCGAGTCTAGAACTAGTGGATCCCCCGGGCTGCAGGAATTCTGATGG
CTCTCAAAATTCCTGCCTCCTTTAGGGATAAAAGACTTTAAGACTTTTTAACAAAAAAGAAAAAGAAA
AAAAAAATTCCTGCCTCCTGGTGTACACACACAGAAGGGTTCCCTCCCCTTGAATGTGACCAGGATCT
GTGAAAATAACGGGATAGCCGCTCCTGTGATTAGGTTATGTGGTAGACTAGAGCAAGATTCTCCTGCT
GGTTTTGAAGAAGTCAGCTGCCATGTTGTGAGACTGTCATGGGCTAGGGCATGAGCCTTTAAATATCT
GGGAGCAACCCCTGGCCAGCAGCCAGTGAGAAAACGGGCCCTCAGTCCTACAATCACAAGGAACTAA
ATTCTGCCAACAACCTGAAGGAACTTTGAAGAGGATCATGAGTCCCTTGATTCAGCTTGATGAGCCCC
TGAGCAGAGGATACAGCTAACTTGTACTAGGGAAGTATAAAAAACATGCATGGGAATGATATATATC
AACTTTAAGGATAATTGTCATACTTCTGGGAATGAAGGGAAAGAAATGGGGCTTTAGTTGTATTATGA
TCTTTAATTTCTCAAAAAAAATAAGATCAGAAGCAAATATGGCAAAATGTTAATACTTTTGTGGGTAC
GTAGGTATTCAGCATACCCTTTTTTCTGAGTTCAAAATATTTTATAATTAAAATGAAATGCAGGCCAGG
CACAGTGGCTCATGCCTATAATACCAGCACTTTGCGAGGCCGAGGTGGGAGGATGGCTTGAGGCCAGA
CCAGCCTGGCCAACATGGCAAAACCCCATCTCTACTTAAAAAAAAAAAAAACTATATATATATATATGT
GTGTGTGTGTATATATATATATGTATATATATTTATATATGTGTGTATATATATATATGTATATATAT
TTATATATGTGTGTGTATATATATATATACACACACACACATATATACATACATACATACACACACACA
CACACACAATTAGCCAGGCATGGTGGCGCACACCTGTAGTCCCAGCTACTTGGGAGGCTGAGACATGA
GAATTGCTTGAACCTGGGAGGCAGAGTAGTTAGTGAGCTGAGATCATACCACTGCACTCCAGCCTGGT
GACAGAGTGAGACTCTGTCTTAAAAAAAATAAAAATTAAAATTAAATGCAAAAGGTCCAAGTGAATT
GAAGAGGAAAGGGGTATCAAGGAAGGTTTTGTGGAGGTGACGTTTGAGCTGGGTCTTAAATGACTTA
AACATGGGATAAGAAGGGAGGGAATAAGGACATTTCAGGTACGAGAAATAAGGAGCATCAGTGGAA
ACAACCTAACGTCTGTCAACCAGTGAATGGATAACAAAATGTAATTCAGATGGTATCCAACTTACGA
TGGTTCCAACATGAGATTTTTCTGACTTTAGGATAGATTTATCAAAGTAGTAAATCCATTTTCAACTTA
TGATATTTTCAACTTCAGATGGGTTTATCAGGACACAGTTGAGGAACACCTGTCTATCCATACAATTTG
GCAATAAAAAGGAAATGAGTGCAGATATACTCCACAACATGAATGAACCTTGAAAACATTAAGTGAG
AGAAGCCAGATACAAAAGGCCACATATTGTATGATTCTATTTATACAAAATGTCCAGAATAGGCAAAT
CTTATAGACAGCAAGTAGGTAGATGATCAGTTTGCTAGGTGCTGGGGGAAGGGGAAATGGGGAGTGA
TGGCTAAGGGGATTGGGTTTCTTTGTGGGGAAATGAAAATGTTTTAAAATTGAGCGTGATAATGATTG
CTCAATGCTGCATATATATATAATCTATAGATTATATATATATAAAGAGAGGCTGTTAGACAGTGATA
AGTGATATATATATATATACATAGAGAGAGAGAGAGAGAGAGAGAGAGGCTGTTAGTGATAAGTG
ATCAGGAAAATAAAAGTATTGAGGAGGAATACGAAGTTGACGGTGTGAAAACATGAGATTTTATATA

FIG. 2

```
GGATGGCCAGGGAAGGCCTTAATGAGAAAGTGACTTATGAGTAAAAACAAGGGATCCTAAACCTTAG
CATGCATCAGAATCACTCGGAAACTTGTTAAAGCATAGCTTGCTGGGCCTCATCACAGATATTTTGATT
CGGTAGGTTCTTGTCTGATATTAATACTTTTGGTCTAGGGAACCACATTTTGAGAACCACTGAGCTAAA
GGAAGTAAAGGTTTCCCTTAGTTTACTAGCTGGTAACCCTAGGAAACTGCTTAGCCTCTCGGTGCTAAG
ATACAAAATACTTTAGCACATAATAACACATGGAAAATAGTCTATAAATTATAAATATTATTTTTATG
TACCAAATATTACATAAGACAAAATCTAAGCAAGATATATATATATACATAAAATATAAGATATAT
ATGTATATATTATATATAGATAAATAGAGAGAGAGAGTTATGTTTAGAAAGAAAATACTTCAAACTAA
AAAAAGAGAGGTAGGAAGTATACCATTCCATTATTGGTAAAAACAAATTACTAAGTAGTCTTTACAAA
AAACCAATCTCACTCCTTTAGAACACAAGCCCACCATTAAAACTGATGCAGAGGAATTTCTCTCCCTG
GCTTACCTTTAGGATGGTGCATACTAAGTTAGAAAAGTCATAAATGTTATATTAAAAGTAAATGTGAA
CTTACTTCCACAATCAAGACATTCTAGAAGAAAAAGAGAAATGAAAATCAGTACAATGAATAAAACG
GTATTTCCAATTATAAGTCAAATCACATCATAACAACCCTAAGGAATTATCCAAACTCTTGTTTTTAGA
TGCTTTATTATATCAAACTCTCCTTTAAACAAGTGGCCCATCTGCTGGGATTTGGAAGCCTGTAATACT
GAAATTTTCATCATAATGGAAATTTTAAAAACAGAATTTGACCCACCTGTTTTTAAAACACTTTCATTA
CTTAACAAGAGGTCTAATCTTGGGCAAGTCTTGAAATTTCTCTGGCCTTAGTTTCCCATGTGTTAAATG
AAACTTGAAGCAGTTGGTCTCTTTATAGTCTCCTGACTCTAACATTCTAAGAATTATATTTGTACAATAA
CTCAAAAATCACATAATTTAATTTACCATATGGACTCCAAAATATATTTTCTCATTAGGCTAAACTTGA
TCTGCATTTTCTGGATGTGTCCATATTCTTGGACTACACTAAAACATGATACCAATGCTTCCTCTCACC
ATAAACCCTCACTTCGCTTTCTACATTTAAGAATTTTATAGCTGGAAGAGTCCTTAACAGAAAATACCA
TCTAATAATTACCCCTCAAAATCGAGAAAGTCCTATCTGTTCTTATGCTAGTTATAAGAATGAGGCAGC
ATTTCACATAATGGTTATAAACACTGCCACAAGAAGATTCATGATGTGTTGTTTATCTGTAGCTCTCAT
CATACTCTGTCATATAACTATAGCATTAAGATTTTAATGTTCTATATATTCTTCTAAGACAGTGTTTACC
AGAGTAAGGCACAAAAGATCCACTGGTTTGCAAGAAAGATTAGAACTTTTAAATTTTTTAACCTCACC
TTGTTTAATCTATATTTTTGTATGTATTTTGTAACATATATATTATTATTACCATAAATCATATATAATTT
AAAATGCATATATTAGGGGTAAATGCTCAGGAAACTTTTTATAAATTGGGCATGCAAATACAAGTTTG
AAGACTCACTGTTCTAGGTATTAAAAGTAAAGTTATAACCAAGTAAAGCTTCCACCTTTTCATGTCTCA
AAGCAGTTTATTGTTGGAGGTAAGATCTCTTAGAAGCCTAAACAGGTCCAAGTACAGAATGAAGTAAG
GCTAGCCCATAACTTGTGGCAAGCAATTCATACTATTTCTCTCATGCTGAGCTCTCCTCAGTGAAGCAG
CTACTATAGACAACTGCAGCCTATTGGTAGCCTATTTTACAGGCAGGAAAAAAATTACTTTTTATTCA
AAGTGGAACTCAGGACATGGGGAGAAAATGAATACAAAAAATAGGGTCAATCCAAAGGCACACAGC
AAATGAGTAACACAGTTATGTTTTTTTCCCATTTGTATGAGGTCCCAGTAAATTCTAAGTAAACTGCAA
ATTTAATAATACACTAAAAAAGCCATGCAATTGTTCAAATGAATCCCAGCATGGTACAAGGAGTACAG
ACACTAGAGTCTAAAAAACAAAAGAATGCCATTATTGAGTTTTTGAATTATATCAAGTAGTTACATCT
CTACTTAATAAATGAGAAAAACGAGGATAAGAGGCCATTTGATAAAATGAAAATAGCCAAGAAGTGG
TATTAGAGACTTGAATACAGGTATTCGGGTCCAAAGTTCATCTGCTCAAATACTAACTGGGGAAAAGA
GGGAAAAATATTTATATACATATATATCTGCACACAAAAATACCCCCAAAAGACAAAATGAGGCCAG
GCAGGGTGGCTCACACCCGTAATCCCGGTACTTTGGGAGGCTGAGGCAGGTGGATACCTGAGATCAGG
```

FIG. 2A

```
AGTTGGAGATCAGCCTGGTCAACATGGTGAAACCCTGTCTCTACTAAAGATAAAAAAATTAGCCAGGC
ATGGTGGCGTGCGCCTGTAATCCCAGCTACTTGGGAGTCTGAGGCAGGAGAATCACTTGAACTGGGAA
GGGGAGGTTGCAGTGAGCCAAGATCGTACTACTGCACTCCAGCCTGGGCAGCAGAGTGAGACTCCATC
ACAAAAATAAATAAATAAATAAAATACAATGAAACAGAAAGTTCAAATAATCCCATAATCTTACCAC
CAAGAAATAACTTTCACTCGTTATACTTATTGATTTTTCCATAATAAATGTACTTTACTGTGACTATCAT
GAAAAGAAAGTTATTTTAGAAACAGAGAACTGTTTCAGATCAAATCTATGTAGTAGAACAGAGCCATT
AGGTGGGAAAGACGAGATCAAACTAAATCTCAGAAGGCCTAAAAGGCTAGGTCCATTCCAGCACTAA
AAACTGACCAGACAAGTAATGGCTTCAACAGCTTCTAAATATGGACAAAGCATGCTGAAAGGGAAGG
ACAGGTCTAACAGTGGTATATGAAATGAACAGGAGGGGCAAAGCTCATTTCTCCTCTGAAGTTTTCCA
AAGATGCTGAGGAGGACATTAGTTTGACATGACCCTGATATGGGACAAGATAATTTCACAGAAGTTTT
ACATGTTAAAGTTTTCTTATAGATACTCATTCAAGTAAGCAATGAACACTAAAATCTAAAGAAAGAAA
AGAGCTTTAGAGTCAGGTCTGTATTCAAATTCAAGCTCTACCACTTACTGGTTCTGTGACTTTGGGCAA
GTCTTTTAACCTTATTAAGTCTTAATTTCCTGATTTGTAAAATGGGGATATCGTCTCCCTCACAGGATTG
TTGTGAAACTTTTATGAGATTAATGCCTTTATATTTGGCATAGTGTAAGTAAACAATAACTGGCAGCTT
CAAAAAAAAAAAAGCAGTAGCATTCCATCATTTATTATTGGTTACTCTCAAAAAGTTTTTCAATGTACTA
GAAGATAAATATTCAAATACCTTAATATCTCCATTATTTTCAGGTAAACAGCATGCTCCTGAACAACCA
ATGGGTCAACAAATAAATTAAAAGGGAAATCTAAAAACATCTTGATATTAAACTACATGGAAGCACA
ATATACCAAAACCAATGGTTCACACTAGGAGAATTTTAAGGTACAAGAAAACTCTTTGAGATTTCTTA
AAATAATAGTATGTCTGAATTTATTGAGTGATTTACCAGAAACTGTTGTAAGAGCTCTACTTGCATTAT
AGCACTTAATCCTCTTAACTCTATGGCTGCTATTATCAACCTCACCCTAATCACATATGGGACACAGAG
AGGTTAAGTAACTTGCCCAAGGTCAGAGTTAGGAAGTACTAAGCCATGCTTTGAATCAGTTGTCAGGC
TCCGGAACTCACACTTTCAGCCACTACATAATACTGCTTTGCTATCTTTTAGGAAACTATGTGAGTCTA
CCTCACATAGACTCACATAGGTTTGTTTTTTTTTTTTTTAAAGGCTATCTTTTCCCCCATCAATGTTTT
TTGAAGGATCCCAAATTAGAGTCCCACAGAGGCAGACAGCAGTACTTGACAATATGGACATTTAAGGT
TAATGTTGGATTCTACTGTCTTTTTACTACATGACCTAGGGAACGATAATTAACCTAGACTGCTTCCAA
GGGTTAAATAACCCATTTAGTTATACTATGTAAATTATCTCTTAGTGATTGATTGAAAGCACACTGTTA
CTAATTGACTCGGTATGAAGTGCTTTTTTTTCTTCCCTTTCAAGATACATACCTTTCCAGTTAAAGTTGA
GAGATCATCTCCACCAATTACTTTTATGTCCCCTGTTGACTGGTCATTCTAGTTAAAAAAAAAAAAACT
ATATATATATATATCTACACACACATATGTATATGTATATCCTTATGTACACACACAAACTTCAAATTA
AATGAGAACTAGAAGATTTGAGAAGTTAGCTAGCTAATATCCATAGCATTATGATATTCTAAATGATA
TGAATTATAAGAATTAGGTTTCCTGAAATGAATGACTAGAAAACTTTCAAGTAGAGATTAGTAAAAAT
TAAAAAGTCCTAATCGGCCATTACTGATTTGATGTTTTTAAGAGTCCTAAAAAATGGGTTACATCCATT
TTTAAGTGGGTAGTATTATAACAGCCACCCATCTTCAATCACAGTGATTTCTGAATTGTGAGGGAAGTT
ATTAGCATGACAGGTGTCTGGTTCTGGCCCTGTACGATTCCCATGAGTCAAGCAAATTGTAAGGGCTG
GTCTATATCACACCCAACCCCAAGGATATGTCCCTCAAAAGTCTAGCCCAGGCCCCGTCATCTTCAGC
ATCATCTGGGAAACCAGGTCTGATTAGTAGTCCTTTAAGGAATACCTCTTAGGCTCCCATTTTACTGCT
ATCACAGAATCCAATAAAACCCTTACAGGAGATTCAATGGGAAATGCTCAACACCCACTGTAGTTGGT
```

FIG. 2B

```
GGTGACAATGACCATAATTTGGCTGTGCTGGATTCAGGACAGAAAATTTGGGTGAAAGAGCAGGTGA
ACAAAAGAGCTTCGACTTGCCCTAGCAGAGAGCAAGCCATACCATACCACAAAGCCACAGCAATTAC
AACGGTGCAGTACCAGCACAGTAAATGAACAAAGTAGAGCCCAGAAACAGACCCAGAACTATATGAG
GATTTAGTATACAATAAAGATGGTATTTCGAGTCAGTAGGGAAAAGATGAATTATTCAATAAATGATG
TTTGGCCAACTAGTAACCCATTTGGGAAAAAATAAAAGTATGGTCCCTACCTCACAGCATACACAAAA
ATAAATTCCAGACGGATTAAAATCTAAATGTAAAAAATAAAGCCATAAGTGGACTGGAAGAAAATAG
AGAATTTTTTTTAACATCCGTAGAAAGGGTAAAAACCCAGGCATGACATGAACCAAAACTGAAGAGG
TTCTGTAACAAATACCCCCTTTTATATATTGGGCTCCAACAATAAGAACCCATAGGAAAATGGAGAAT
GAACACAAATAGACAATTTATAGAAGAGAAGGTTATAAGGTGTAAAATTATATCTATCTGAGAAACA
AACACTAAAACAATGTGATTCTACTGTTCTCCCACCCATACTGGCAAAACTTAAGCCTGATAATATGCT
GAGGGGAAATAAGCACTCTTGTTGGTGAGAGTATTAATTGGCATAGCTTCTTTTGAAAATGACATAGC
AATACCTGTTAAAATTGCAAACATGCATGTCACTTAATTCCATGTAATTCCCACTTCTGGGAATCAATT
GCTACAAAAACACTTGACAAGTATACAAAGATACATTCAAGAGTGTTCACTGGGCCGGGTGCGGTGGC
TTCATGCCTGTAATCCCAGGGAGGCAGAGGCAAGACGATCGCTTGACCCCAGGAGTTCAAGGCCAGCC
CGAGAAACACAGCAAGACCCTGTCTCTCTTTTTTTTATTTAAAAAATAAATGTTCACTGTATCAGTTGT
TCACAAAAACAAACCAACATGTCCATTAACAGGGAACCATTTAAATTAATCAAGTTCATCTACACAAT
GTAATACCATGCAACTATTAAAAAGCACCTGATAATCCAAAGCACACTGAGACAGAATAATGCTATTA
AAAACACCAAGTAGTGGAACACTGTGTTGCCTATGACACCATTTTTATTCAACATTTAAACAAATTTGT
AACAGCAATTACATGAGTAGTGACAATGGCGTTTATGAGACTTTTCACTTTTATGTGCTTCTATTTTTGT
TATGCTTCTATATATACATCCATTTATTATGGAGTGTTACTTTCAAAAATCACAAATGGGCCAGTATTA
TTTGGTGTTGCAAGGTGAGCATATGACTTCTGATATCAACCTTTGCATATTACTTCTCAATTTAGGGAA
ATTACAGACATCCCTTATTCTAACTAACTTAAAACCCAGCATTTCAAACATACAGAATTGATGGGGAA
AAAAAGAAAGAAGAAAGAAAGAAAAGGCAACAAGCTTCAGATGACAGTGACTCACATCAAATTATT
TATAAAATCTGTTAAATAGTGCCATCTTCTGGAGATACCTGGTATTACAGTCCAACTCCAGTTGATGTC
TTTACAGAGACAAGAGGAATAAAGGAAAAAATATTCAAGAACTGAAAAGTATGGAGTCATGGAAAAA
TTGCTGTGATCCAAAGGCTACGGTGATAGGACAAGAAACAAGAGAACTCCAAGCAGTAAGACACTGC
TGTTCTATTAGCATCCAAACCTCCATACCTCCTGTTTGCCCCAAGGCTTTTTTAAAAAATAGAGACAGG
ATCTCACTATTTTGCTCAGGCTGGTCTTGAACTCCTGGACTCAAGCTATCCTCCTGCCTCGGCCTCCTAA
AGTGCCGAGATTACAGGCTTGAGTCACCATACCTGGCTATTTATTTTTTCTTAACTCTCTTGCCTGGCCT
ATAGCCACCATGGAAGCTAATAAAGAATATTAATTTAAGAGTAATGGTATAGTTCACTACATTGGAAT
ACAGGTATAAGTGCCTACATTGTACATGAATGGCATACATGGATCAATTACCCCACCTGGGTGGCCAA
AGGAACTGCGCGAACCTCCCTCCTTGGCTGTCTGGAACAAGCTTCCCACTAGATCCCTTTACTGAGTGC
CTCCCTCATCTTTAATTATGGTTAAGTCTAGGATAACAGGACTGGCAAAGGTGAGGGGAAAGCTTCCT
CCAGAGTTGCTCTACCCTCTCCTCTACCGTCCTATCTCCTCACTCCTCTCAGCCAAGGAGTCCAATCTGT
CCTGAACTCAGAGCGTCACTGTCAACTACATCAAAATTGCCAGAGAAGCTCTTTGGGACTACAAACAC
ATACCCTTAATGTCTTTATTTCTATTTTGTCTACCTCTTCAGTCTAGGTGAAAAAATAGGAAGGATAAT
AGGGAAGAACTTTGTTTATGCCTACTTATCCGCCCCTAGGAATTTTGAAAACCTCTAGGTAGCAATAA
```

FIG. 2C

```
GAACTGCAGCATGGTATAGAAAAAGAGGAGGAAAGCTGTATAGAAATGCATAATAAATGGGCAGGA
AAAGAACTGCTTGGAACAAACAGGGAGGTTGAACTATAAGGAGAGAAAGCAGAGAGGCTAATCAAC
AAGGCTGGGTTCCCAAGAGGGCATGATGAGACTATTACTAAGGTAGGAATTACTAAGGGCTCCATGTC
CCCTTAGTGGCTTAGTACTATGTAGCTTGCTTTCTGCAGTGAACTTCAGACCCTTCTTTTAGGATCCTAG
AATGGACTTTTTTTTTTTATCGGAAAACAGTCATTCTCTCAACATTCAAGCAGGCCCCAAGTCTACCAC
ACTCAATCACATTTTCTCTTCATATCATAATCTCTCAACCATTCTCTGTCCTTTTAACTGTTTTTCTATAC
CCTGATCAAATGCCAACAAAAAGTGAGAATGTTAGAATCATGTATTTTTAGAGGTAGACTGTATCTCA
GATAAAAAAAAGGGGCAGATATTCCATTTTCCAAAATATGTATGCAGAAAAAATAAGTATGAAAGG
ACATATGCTCAGGTAACAAGTTAATTTGTTTACTTGTATTTTATGAATTCCCTAAAACCTACGTCACCC
GCCCCGTTCCCACGCCCCGCGCCACGTCACAAACTCCACCCCCTCATTATCATATTGGCTTCAATCCAA
AATAAGGTATATTATTGATGATGTTAATTAACATGCATGGATCCATATGCGGTGTGAAATACCGCACA
GATGCGTAAGGAGAAAATACCGCATCAGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGG
GGATAACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTGCAGCCA
TGAGATTATCAAAAAGGATCTTCACCTAGATCCTTTTCACGTAGAAAGCCAGTCCGCAGAAACGGTGC
TGACCCCGGATGAATGTCAGCTACTGGGCTATCTGGACAAGGGAAAACGCAAGCGCAAAGAGAAAGC
AGGTAGCTTGCAGTGGGCTTACATGGCGATAGCTAGACTGGGCGGTTTTATGGACAGCAAGCGAACCG
GAATTGCCAGCTGGGGCGCCCTCTGGTAAGGTTGGGAAGCCCTGCAAAGTAAACTGGATGGCTTTCTT
GCCGCCAAGGATCTGATGGCGCAGGGGATCAAGCTCTGATCAAGAGACAGGATGAGGATCGTTTCGC
ATGATTGAACAAGATGGATTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGTCAGCGCAGGGGCGCCCGG
```

FIG. 2D

TTCTTTTTGTCAAGACCGACCTGTCCGGTGCCCTGAATGAACTGCAAGACGAGGCAGCGCGGCTATCG
TGGCTGGCCACGACGGGCGTTCCTTGCGCAGCTGTGCTCGACGTTGTCACTGAAGCGGGAAGGGACTG
GCTGCTATTGGGCGAAGTGCCGGGGCAGGATCTCCTGTCATCTCACCTTGCTCCTGCCGAGAAAGTAT
CCATCATGGCTGATGCAATGCGGCGGCTGCATACGCTTGATCCGGCTACCTGCCCATTCGACCACCAA
GCGAAACATCGCATCGAGCGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGGCGAGCATGCCCGACGGC
GAGGATCTCGTCGTGACCCATGGCGATGCCTGCTTGCCGAATATCATGGTGGAAAATGGCCGCTTTTCT
GGATTCATCGACTGTGGCCGGCTGGGTGTGGCGGACCGCTATCAGGACATAGCGTTGGCTACCCGTGA
TATTGCTGAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAATTTTGTTAAAATTTTTGTTAAAT
CAGCTCATTTTTTTAACCAATAGGCCGAAATCGGCAAAATCCCTTATAAATCAAAAGAATAGACCGAGA
TAGGGTTGAGTGTTGTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAATCAAGTTTTTTGGG
GTCGAGGTGCCGTAAAGCACTAAATCGGAACCCTAAAGGGAGCCCCCGATTTAGAGCTTGACGGGGA
AAGCCGGCGAACGTGGCGAGAAAGGAAGGGAAGAAAGCGAAAGGAGCGGGCGCTAGGGCGCTGGCA
AGTGTAGCGGTCACGCTGCGCGTAACCACCACACCCGCCGCGCTTAATGCGCCGCTACAGGGCGCGTC
CATTCGCCATTCAGGATCGAATTAATTCTTAATTAA

FIG. 2E

SEQ ID NO:2 Human TM amino acid sequence

MLGVLVLGALALAGLGFPAPAEPQPGGSQCVEHDCFALYPGPAT
FLNASQICDGLRGHLMTVRSSVAADVISLLLNGDGGVGRRRLWIGLQLPPGCGDPKR
LGPLRGFQWVTGDNNTSYSRWARLDLNGAPLCGPLCVAVSAAEATVPSEPIWEEQQ
CEVKADGFLCEFHFPATCRPLAVEPGAAAAVSITYGTPFAARGADFQALPVGSSAA
VAPLGLQLMCTAPPGAVQGHWAREAPGAWDCSVENGGCEHACNAIPGAPRCQCPA
GAALQADGRSCTASATQSCNDLCEHFCVPNPDQPGSYSCMCETGYRLAADQHRCED
VDDCILEPSPCPQRCVNTQGGFECHCYPNYDLVDGECVEPVDPCFRANCEYQCQPLN
QTSYLCVCAEGFAPIPHEPHRCQMFCNQTACPADCDPNTQASCECPEGYILDDGFICT
DIDECENGGFCSGVCHNLPGTFECICGPDSALARHIGTDCDSGKVDGGDSGSGEPPPS
PTPGSTLTPPAVGLVHSGLLIGISIASLCLVVALLALLCHLRKKQGAARAKMEYKCAA
PSKEVVLQHV RTERTPQRL

FIG. 3

SEQ ID NO:3  human TM nucleotide sequence atgcttggg gtcctggtcc ttggcgcgct ggccctggcc ggcctggggt tccccgcacc cgcagagccg cagccgggtg
gcagccagtg cgtcgagcac gactgcttcg cgctctaccc gggcccccgcg accttcctca atgccagtca gatctgcgac
ggactgcggg gccacctaat gacagtgcgc tcctcggtgg ctgccgatgt catttccttg ctactgaacg gcgacggcgg
cgttggccgc cggcgcctct ggatcggcct gcagctgcca cccggctgcg gcgaccccaa gcgcctcggg cccctgcgcg
gcttccagtg ggttacggga gacaacaaca ccagctatag caggtgggca cggctcgacc tcaatggggc tccctctgc
ggcccgttgt gcgtcgctgt ctccgctgct gaggccactg tgcccagcga gccgatctgg gaggagcagc agtgcgaagt
gaaggccgat ggcttcctct gcgagttcca cttcccagcc acctgcaggc cactggctgt ggagcccggc gccgcggctg
ccgccgtctc gatcacctac ggcaccccgt tcgcggcccg cggagcggac ttccaggcgc tgccggtggg cagctccgcc
gcggtggctc ccctcggctt acagctaatg tgcaccgcgc cgcccggagc ggtccagggg cactgggcca gggaggcgcc
gggcgcttgg gactgcagcg tggagaacgg cggctgcgag cacgcgtgca atgcgatccc tggggctccc cgctgccagt
gcccagccgg cgccgccctg caggcagacg ggcgctcctg caccgcatcc gcgacgcagt cctgcaacga cctctgcgag
cacttctgcg ttcccaaccc cgaccagccg ggctcctact cgtgcatgtg cgagaccggc taccggctgg cggccgacca
acaccggtgc gaggacgtgg atgactgcat actggagccc agtccgtgtc cgcagcgctg tgtcaacaca cagggtggct
tcgagtgcca ctgctacccct aactacgacc tggtggacgg cgagtgtgtg gagcccgtgg acccgtgctt cagagccaac
tgcgagtacc agtgccagcc cctgaaccaa actagctacc tctgcgtctg cgccgagggc ttcgcgccca ttccccacga
gccgcacagg tgccagatgt ttgcaacca gactgcctgt ccagccgact gcgaccccaa cacccaggct agctgtgagt
gccctgaagg ctacatcctg gacgacggtt tcatctgcac ggacatcgac gagtgcgaaa acggcggctt ctgctccggg
gtgtgccaca acctccccgg taccttcgag tgcatctgcg ggcccgactc ggcccttgcc cgccacattg gcaccgactg
tgactccggc aaggtggacg gtggcgacag cggctctggc gagcccccgc ccagcccgac gccggctcc accttgactc
ctccggccgt ggggctcgtg cattcgggct tgctcatagg catctccatc gcgagcctgt gcctggtggt ggcgcttttg
gcgctcctct gccacctgcg caagaagcag ggcgccgcca gggcaagat ggagtacaag tgcgcggccc cttccaagga
ggtagtgctg cagcacgtgc ggaccgagcg gacgccgcag agactc

FIG. 4

SEQ ID NO: 4

```
GTTTAAACGGGCCCTCTAGACGCGTTGACATTGATTATTGACTAGTTATTAATAGTAATCAATTACGGG
GTCATTAGTTCATAGCCCATGATATCATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAA
TAGGGACTTTCCATTGACGTCAATGGGTGGAGTATTTACGGTAAACTGCCCACTTGGCAGTACATCAA
GTGTATCATATGCCAAGTACGCCCCCCTATTGACGTCAATGACGGTAAATGGCCCGCCTGGCATTATG
CCCAGTNCATGACCTTATGGGACTTTCCTACTTGGCAGACATCTACGTATTAGTCATCGCTATTACCAT
GGTGATGCGGTTTTGGCAGTACATCAATGGGCGTGGATAGCGGTTTGACTCACGGGGATTTTCCAAGT
CTCCACCCCATTGACGTCAATGGGAGTTTGTTTTGGCACCAAAATCAACGGGACTTTCCAAAATGTCGT
AACAACTCCGCCCCATTGACGCAAATGGGCGGTAGGCGTGTACGGTGGGAGGTCTATATAAGCAGAG
CTCTCTGGCTAACTAGAGAACCCCTGCTTACTGGCTTATCGAGATATCTGCAGAATTCATCTGTCGACT
GCTACCGGCAGCGCGCAGCGGCAAGAAGTGTCTGGGCTGGGACGGACAGGAGAGGCTGTCGCCATCG
GCGTCCTGTGCCCCTCTGCTCCGGCACGGCCTGTCGCAGTGCCCGCGCTTTCCCCGGCGCCTGCACGC
GGCGCGCCTGGGTAACATGCTTGGGGTCCTGGTCCTTGGCGCGCTGGCCCTGGCCGGCCTGGGGTTCC
CCGCACCCGCAGAGCCGCAGCCGGGTGGCAGCCAGTGCGTCGAGCACGACTGCTTCGCGCTCTACCCG
GGCCCCGCGACCTTCCTCAATGCCAGTCAGATCTGCGACGGACTGCGGGGCCACCTAATGACAGTGCG
CTCCTCGGTGGCTGCCGATGTCATTTCCTTGCTACTGAACGGCGACGGCGGCGTTGGCCGCCGGCGCCT
CTGGATCGGCCTGCAGCTGCCACCCGGCTGCGGCGACCCCAAGCGCCTCGGGCCCCTGCGCGGCTTCC
AGTGGGTTACGGGAGACAACAACACCAGCTATAGCAGGTGGGCACGGCTCGACCTCAATGGGGCTCC
CCTCTGCGGCCCGTTGTGCGTCGCTGTCTCCGCTGCTGAGGCCACTGTGCCCAGCGAGCCGATCTGGGA
GGAGCAGCAGTGCGAAGTGAAGGCCGATGGCTTCCTCTGCGAGTTCCACTTCCCAGCCACCTGCAGGC
CACTGGCTGTGGAGCCCGGCGCCGCGGCTGCCGCCGTCTCGATCACCTACGGCACCCCGTTCGCGGCC
CGCGGAGCGGACTTCCAGGCGCTGCCGGTGGCAGCTCCGCCGCGGTGGCTCCCCTCGGCTTACAGCT
AATGTGCACCGCGCCGCCCGGAGCGGTCCAGGGGCACTGGGCCAGGGAGGCGCCGGGCGCTTGGGAC
TGCAGCGTGGAGAACGGCGGCTGCGAGCACGCGTGCAATGCGATCCCTGGGGCTCCCCGCTGCCAGTG
CCCAGCCGGCGCCGCCCTGCAGGCAGACGGGCGCTCCTGCACCGCATCCGCGACGCAGTCCTGCAACG
ACCTCTGCGAGCACTTCTGCGTTCCCAACCCCGACCAGCCGGGCTCCTACTCGTGCATGTGCGAGACC
GGCTACCGGCTGGCGGCCGACCAACACCGGTGCGAGGACGTGGATGACTGCATACTGGAGCCCAGTC
CGTGTCCGCAGCGCTGTGTCAACACACAGGGTGGCTTCGAGTGCCACTGCTACCCTAACTACGACCTG
GTGGACGGCGAGTGTGTGGAGCCCGTGGACCCGTGCTTCAGAGCCAACTGCGAGTACCAGTGCCAGCC
CCTGAACCAAACTAGCTACCTCTGCGTCTGCGCCGAGGGCTTCGCGCCCATTCCCCACGAGCCGCACA
GGTGCCAGATGTTTTGCAACCAGACTGCCTGTCCAGCCGACTGCGACCCCAACACCCAGGCTAGCTGT
GAGTGCCCTGAAGGCTACATCCTGGACGACGGTTTCATCTGCACGGACATCGACGAGTGCGAAAACGG
CGGCTTCTGCTCCGGGGTGTGCCACAACCTCCCCGGTACCTTCGAGTGCATCTGCGGGCCCGACTCGGC
CCTTGCCCGCCACATTGGCACCGACTGTGACTCCGGCAAGGTGGACGGTGGCGACAGCGGCTCTGGCG
AGCCCCGCCCAGCCCGACGCCCGGCTCCACCTTGACTCCTCCGGCCGTGGGGCTCGTGCATTCGGGC
TTGCTCATAGGCATCTCCATCGCGAGCCTGTGCCTGGTGGTGGCGCTTTTGGCGCTCCTCTGCCACCTG
CGCAAGAAGCAGGGCGCCGCCAGGGCCAAGATGGAGTACAAGTGCGCGGCCCCTTCCAAGGAGGTAG
TGCTGCAGCACGTGCGGACCGAGCGGACGCCGCAGAGACTCTGAGCGGCCTCCGTCCAGGAGCCTGG
CTCCGTCCAGGAGCCTGTGCCTCCTCACCCCCAGCTTTGCTACCAAAGCACCTTAGCTGGCATTACAGC
TGGAGAAGACCCTCCCCGCACCCCCCAAGCTGTTTTCTTCTATTCCATGGCTAACTGGCGAGGGGGTG
ATTAGAGGGAGGAGAATGAGCCTCGGCCTCTTCCGTGACGTCACTGGACCACTGGGCAATGATGGCAA
TTTTGTAACGAAGACACAGACTGCGATTTGTCCCAGGTCCTCACTACCGGGCGCAGGAGGGTGAGCGT
TATTGGTCGGCAGCCTTCTGGGCAGACCTTGACCTCGTGGGCTAGGGATGACTAAAATATTTATTTTTT
TTAAGTATTTAGGTTTTTGTTTGTTTCCTTTGTTCTTACCTGTATGTCTCCAGTATCCACTTTGCACAGCT
CTCCGGTCTCTCTCTCTCTACAAACTCCCACTTGTCATGTGACAGGTAAACTATCTTGGTGAATTTTTTT
TTCCTAGCCCTCTCACATTTATGAAGCAAGCCCCACTTATTCCCCATTCTTCCTAGTTTTCTCCTCCCAG
GAACTGGGCCAACTCACCTGAGTCACCCTACCTGTGCCTGACCCTACTTCTTTTGCTCTTAGCTGTCTG
CTCAGACAGAACCCCTACATGAAACAGAAACAAAAACACTAAAAATAAAAATGGCCATTTGCTTTTTC
ACCAGATTTGCTAATTTATCCTGAAATTTCAGATTCCCAGAGCAAAATAATTTTAAACAAAGGTTGAG
ATGTAAAAGGTATTAAATTGATGTTGCTGGACTGTCATAGAAATTACACCCAAAGAGGTATTTATCTTT
ACTTTTAAACAGTGAGCCTGAATTTTGTTGCTGTTTTGATTTGTACTGAAAAATGGTAATTGTTGCTAA
```

FIG. 5

```
TCTTCTTATGCAATTTCCTTTTTTGTTATTATTACTTATTTTTGACAGTGTTGAAAATGTTCAGAAGGTT
GCTCTAGATTGAGAGAAGAGACAAACACCTCCCAGGAGACAGTTCAAGAAAGCTTCAAACTGCATGA
TTCATGCCAATTAGCAATTGACTGTCACTGTTCCTTGTCACTGGTAGACCAAAATAAAACCAGCTCTAC
TGGTCTTGTGGAATTGGGAGCTTGGGAATGGATCCTGGAGGATGCCCAATTAGGGCCTAGCCTTAATC
AGGTCCTCAGAGAATTTCTACCATTTCAGAGAGGCCTTTTGGAATGTGGCCCCTGAACAAGAATTGGA
AGCTGCCCTGCCCATGGGAGCTGGTTAGAAATGCAGAATCCTAGGCTCCACCCCATCCAGTTCATGAG
AATCTATATTTAACAAGATCTGCAGGGGGTGTGTCTGCTCAGTAATTTGAGGACAACCATTCCAGACT
GCTTCCAATTTTCTGGAATACATGAAATATAGATCAGTTATAAGTAGCAGGCCAAGTCAGGCCCTTATT
TTCAAGAAACTGAGGAATTTTCTTTGTGTAGCTTTGCTCTTTGGTAGAAAAGGCTAGGTACACAGCTCT
AGACACTGCCACACAGGGTCTGCAAGGTCTTTGGTTCAGCTAAGCTAGGAATGAAATCCTGCTTCAGT
GTATGGAAATAAATGTATCATAGAAATGTAACTTTTGTAAGACAAAGGTTTTCCTCTTCTATTTTGTAA
ACTCAAAATATTTGTACATAGTTATTTATTTATTGGAGATAATCTAGAACACAGGCAAAATCCTTGCTT
ATGACATCACTTGTACAAAATAAACAAATAACAATGTGAAAAAAAAAAAAAAAAAAAAAAAAAAAA
AAAAAAAAAAAAGGTAGCAGTCGACAGATGAATTCCACCACACTGGACTAGTGGATCCGAGCTCGGT
ACCAAGCTTAAGTTTAAAC
```

FIG. 5A

SEQ ID NO 5

TCTAGACGCGTTGACATTGATTATTGACTAGTTATTAATAGTAATCAATTACGGGGTCATTAGTTCATA
GCCCATGATATCATATGGAGTTCCGCGTTACATAACTTACGGTAAATGGCCCGCCTGGCTGACCGCCC
AACGACCCCCGCCCATTGACGTCAATAATGACGTATGTTCCCATAGTAACGCCAATAGGGACTTTCCA
TTGACGTCAATGGGTGGAGTATTTACGGTAAACTGCCCACTTGGCAGTACATCAAGTGTATCATATGC
CAAGTACGCCCCCCTATTGACGTCAATGACGGTAAATGGCCCGCCTGGCATTATGCCCAGTNCATGAC
CTTATGGGACTTTCCTACTTGGCAGACATCTACGTATTAGTCATCGCTATTACCATGGTGATGCGGTTT
TGGCAGTACATCAATGGGCGTGGATAGCGGTTTGACTCACGGGGATTTTCCAAGTCTCCACCCCATTG
ACGTCAATGGGAGTTTGTTTTGGCACCAAAATCAACGGGACTTTCCAAAATGTCGTAACAACTCCGCC
CCATTGACGCAAATGGGCGGTAGGCGTGTACGGTGGGAGGTCTATATAAGCAGAGCTCTCTGGCTAAC
TAGAGAACCCCTGCTTACTGGCTTATCGAGATATC

FIG. 6

SEQ ID NO 6

GGCAGCGCGCAGCGGCAAGAAGTGTCTGGGCTGGGACGGACAGGAGAGGCTGTCGCCATCGGCGTCC
TGTGCCCCTCTGCTCCGGCACGGCCCTGTCGCAGTGCCCGCGCTTTCCCCGGCGCCTGCACGCGGCGCG
CCTGGGTAACATGCTTGGGGTCCTGGTCCTTGGCGCGCTGGCCCTGGCCGGCCTGGGGTTCCCCGCACC
CGCAGAGCCGCAGCCGGGTGGCAGCCAGTGCGTCGAGCACGACTGCTTCGCGCTCTACCCGGGCCCCG
CGACCTTCCTCAATGCCAGTCAGATCTGCGACGGACTGCGGGGCCACCTAATGACAGTGCGCTCCTCG
GTGGCTGCCGATGTCATTTCCTTGCTACTGAACGGCGACGGCGGCGTTGGCCGCCGGCGCCTCTGGAT
CGGCCTGCAGCTGCCACCCGGCTGCGGCGACCCCAAGCGCCTCGGGCCCCTGCGCGGCTTCCAGTGGG
TTACGGGAGACAACAACACCAGCTATAGCAGGTGGGCACGGCTCGACCTCAATGGGGCTCCCCTCTGC
GGCCCGTTGTGCGTCGCTGTCTCCGCTGCTGAGGCCACTGTGCCCAGCGAGCCGATCTGGGAGGAGCA
GCAGTGCGAAGTGAAGGCCGATGGCTTCCTCTGCGAGTTCCACTTCCCAGCCACCTGCAGGCCACTGG
CTGTGGAGCCCGGCGCCGCGGCTGCCGCCGTCTCGATCACCTACGGCACCCCGTTCGCGGCCCGCGGA
GCGGACTTCCAGGCGCTGCCGGTGGGCAGCTCCGCCGCGGTGGCTCCCCTCGGCTTACAGCTAATGTG
CACCGCGCCGCCCGGAGCGGTCCAGGGGCACTGGGCCAGGGAGGCGCCGGGCGCTTGGGACTGCAGC
GTGGAGAACGGCGGCTGCGAGCACGCGTGCAATGCGATCCCTGGGGCTCCCCGCTGCCAGTGCCCAGC
CGGCGCCGCCCTGCAGGCAGACGGGCGCTCCTGCACCGCATCCGCGACGCAGTCCTGCAACGACCTCT
GCGAGCACTTCTGCGTTCCCAACCCCGACCAGCCGGGCTCCTACTCGTGCATGTGCGAGACCGGCTAC
CGGCTGGCGGCCGACCAACACCGGTGCGAGGACGTGGATGACTGCATACTGGAGCCCAGTCCGTGTCC
GCAGCGCTGTGTCAACACACAGGGTGGCTTCGAGTGCCACTGCTACCCTAACTACGACCTGGTGGACG
GCGAGTGTGTGGAGCCCGTGGACCCGTGCTTCAGAGCCAACTGCGAGTACCAGTGCCAGCCCCTGAAC
CAAACTAGCTACCTCTGCGTCTGCGCCGAGGGCTTCGCGCCCATTCCCCACGAGCCGCACAGGTGCCA
GATGTTTTGCAACCAGACTGCCTGTCCAGCCGACTGCGACCCCAACACCCAGGCTAGCTGTGAGTGCC
CTGAAGGCTACATCCTGGACGACGGTTTCATCTGCACGGACATCGACGAGTGCGAAAACGGCGGCTTC
TGCTCCGGGGTGTGCCACAACCTCCCCGGTACCTTCGAGTGCATCTGCGGGCCCGACTCGGCCCTTGCC
CGCCACATTGGCACCGACTGTGACTCCGGCAAGGTGGACGGTGGCGACAGCGGCTCTGGCGAGCCCCC
GCCCAGCCCGACGCCCGGCTCCACCTTGACTCCTCCGGCCGTGGGGCTCGTGCATTCGGGCTTGCTCAT
AGGCATCTCCATCGCGAGCCTGTGCCTGGTGGTGGCGCTTTTGGCGCTCCTCTGCCACCTGCGCAAGAA
GCAGGGCGCCGCCAGGGCCAAGATGGAGTACAAGTGCGCGGCCCCTTCCAAGGAGGTAGTGCTGCAG
CACGTGCGGACCGAGCGGACGCCGCAGAGACTCTGAGCGGCCTCCGTCCAGGAGCCTGGCTCCGTCCA
GGAGCCTGTGCCTCCTCACCCCCAGCTTTGCTACCAAAGCACCTTAGCTGGCATTACAGCTGGAGAAG
ACCCTCCCCGCACCCCCCAAGCTGTTTTCTTCTATTCCATGGCTAACTGGCGAGGGGGTGATTAGAGGG
AGGAGAATGAGCCTCGGCCTCTTCCGTGACGTCACTGGACCACTGGGCAATGATGGCAATTTTGTAAC
GAAGACACAGACTGCGATTTGTCCCAGGTCCTCACTACCGGGCGCAGGAGGGTGAGCGTTATTGGTCG
GCAGCCTTCTGGGCAGACCTTGACCTCGTGGGCTAGGGATGACTAAAATATTTATTTTTTTTAAGTATT
TAGGTTTTTGTTTGTTTCCTTTGTTCTTACCTGTATGTCTCCAGTATCCACTTTGCACAGCTCTCCGGTCT
CTCTCTCTCTACAAACTCCCCACTTGTCATGTGACAGGTAAACTATCTTGGTGAATTTTTTTTTCCTAGCC
CTCTCACATTTATGAAGCAAGCCCCACTTATTCCCCATTCTTCCTAGTTTTCTCCTCCCAGGAACTGGGC
CAACTCACCTGAGTCACCCTACCTGTGCCTGACCCTACTTCTTTTGCTCTTAGCTGTCTGCTCAGACAG
AACCCCTACATGAAACAGAAACAAAAACACTAAAAATAAAAATGGCCATTTGCTTTTTCACCAGATTT
GCTAATTTATCCTGAAATTTCAGATTCCCAGAGCAAAATAATTTTAAACAAAGGTTGAGATGTAAAAG
GTATTAAATTGATGTTGCTGGACTGTCATAGAAATTACACCCAAAGAGGTATTTATCTTTACTTTTAAA
CAGTGAGCCTGAATTTTGTTGCTGTTTTGATTTGTACTGAAAAATGGTAATTGTTGCTAATCTTCTTATG
CAATTTCCTTTTTTGTTATTATTACTTATTTTTGACAGTGTTGAAAATGTTCAGAAGGTTGCTCTAGATT
GAGAGAAGAGACAAACACCTCCCAGGAGACAGTTCAAGAAAGCTTCAAACTGCATGA
TTCATGCCAATTAGCAATTGACTGTCACTGTTCCTTGTCACTGGTAGACCAAAATAAAACCAGCTCTAC
TGGTCTTGTGGAATTGGGAGCTTGGGAATGGATCCTGGAGGATGCCCAATTAGGGCCTAGCCTTAATC
AGGTCCTCAGAGAATTTCTACCATTTCAGAGAGGCCTTTTGGAATGTGGCCCCTGAACAAGAATTGGA
AGCTGCCCTGCCCATGGGAGCTGGTTAGAAATGCAGAATCCTAGGCTCCACCCCATCCAGTTCATGAG
AATCTATATTTAACAAGATCTGCAGGGGGTGTGTCTGCTCAGTAATTTGAGGACAACCATTCCAGACT
GCTTCCAATTTTCTGGAATACATGAAATATAGATCAGTTATAAGTAGCAGGCCAAGTCAGGCCCTTATT
TTCAAGAAACTGAGGAATTTTCTTTGTGTAGCTTTGCTCTTTGGTAGAAAAGGCTAGGTACACAGCTCT
AGACACTGCCACACAGGGTCTGCAAGGTCTTTGGTTCAGCTAAGCTAGGAATGAAATCCTGCTTCAGT

FIG. 7

```
GTATGGAAATAAATGTATCATAGAAATGTAACTTTTGTAAGACAAAGGTTTTCCTCTTCTATTTTGTAA
ACTCAAAATATTTGTACATAGTTATTTATTTATTGGAGATAATCTAGAACACAGGCAAAATCCTTGCTT
ATGACATCACTTGTACAAAATAAACAAATAACAATGTGAAAAAAAAAAAAAAAAAAAAAAAAAAAA
AAAAAAAAAAAA
```

FIG. 7A

EX VIVO AND IN VIVO EXPRESSION OF THE THROMBOMODULIN GENE FOR THE TREATMENT OF CARDIOVASCULAR AND PERIPHERAL VASCULAR DISEASES

This application claims priority from U.S. Provisional Application Ser. No. 60/430,099 filed Dec. 2, 2002. The entirely of that provisional application is incorporated herein by reference.

FIELD OF THE INVENTION

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND OF THE INVENTION

Atherosclerosis is one of the chief causes of morbidity and mortality in the United States and many other countries of the world. (Zuckerbraun et al., Arch Surg. 137:854–861 [2002]; Kibbe et al., Circ Res. 86:829–33 [2000]). This process can result in limiting the flow of blood to the heart, kidneys and the peripheral vessels, to name a few. Current approaches to the treatment of lesions in the arteries include coronary artery bypass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., Circ Res. 86:829–33 [2000]).

Cardiovascular diseases, however, are the result of complex pathophysiologic processes that involve the expression of many proteins and molecules that can adversely affect the grafted vessel (Shears et al., J. Am Coll Surg., 187(3): 295–306 [1998]; Ross et al., Nature, 362:801–9 [1993]). Approximately 15–30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., Trhomb Haemost., 78:392–95 [1997]). It is a high affinity thrombin receptor that converts thrombin into a protein C activator. Activated protein C then functions as an anticoagulant by inactivating two regulatory proteins of the clotting system, namely factors Va and VI[I]a (Esmon et al., Faseb J., 9:946–55 [1995]). The latter two proteins are essential for the function of two of the coagulation proteases, namely factors Ixa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., Lancet, 353:1729–34 [1999]; Palmer et al., Nature, 327:524–26 [1987]; Kubes et al., PNAS USA., 88:4651–5 [1991]).

Animal studies shown that cytoxic gene transfection utilizing the Herpes Simplex Virus thymydine kinase gene delivered via an adenoviral vector was able to inhibit intimal hyperplasia (Steg et al., Circulation, 96:408–11 [1997]).

Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Bellle et al., Biochem Biophs Res Commun., 235:311–16 [1997]; Salyapongse et al., Tissue Engineering 26(4):663–76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exist a need for a method to effectively introduce therapeutic genes, such as TM, into vascular tissues.

SUMMARY OF THE INVENTION

The present invention relates to a method and composition for treating vascular diseases using gene delivery technologies. One aspect of the present invention relates to a method for treating a vascular disease in a mammal comprising infecting a segment of a blood vessel in vitro using a gutless adenoviral vector which comprises a polynucleotide encoding a thrombomodulin protein or its variant; and grafting the virus-treated blood vessel in said mammal, wherein said thrombomodulin protein or its variant is expressed in a amount sufficient to reduce re-occlusion or intimal hyperplasia in the grafted blood vessel.

Another aspect of the invention relates to a method for treating a vascular disease by evacuating a clot in a blood vessel, isolating a segment of blood vessel around the evacuating site with a balloon catheter and infecting the segment of blood vessel in vivo using a gutless adenoviral vector comprising a polynucleotide encoding a thrombomodulin protein or its variant; wherein the thrombomodulin protein or its variant is expressed in a amount sufficient to reduce re-occlusion or intimal hyperplasia in the infected segment of the blood vessel.

Another aspect of the present invention pertains to a method to administer a therapeutically effective amount of a gutless adenovirus vector into a segment of a blood vessel in vivo using a stent, wherein said gutless adenovirus vector is capable of expressing a thrombomodulin protein or a variant of the thrombomodulin protein.

Yet another aspect of the present invention pertains to a pharmaceutical composition containing a gutless adenovirus capable of expressing thrombomodulin protein or a variant of the thrombomodulin protein and a pharmaceutically acceptable carrier, the gutless adenovirus is produced using a shuttle vector comprising a pBR322 replication origin, a selectable marker gene, an adenovirus left inverted terminal repeat, an adenovirus encapsidation signal, an intronic sequence, and an adenovirus right inverted terminal repeat.

BRIEF DESCRIPTION OF THE FIGURES

FIG. 2 is the DNA sequence (SEQ ID NO: 1) of the gutless backbone shuttle vector.

FIG. 3 is the full length amino acid sequence (SEQ ID NO:2) of human thrombomodulin.

FIG. 4 is the full length DNA sequence (SEQ ID NO:3) encoding human thrombomodulin.

FIG. 5 is the DNA sequence (SEQ ID NO:4) of the expression cassette encoding human thrombomodulin.

FIG. 6 is the DNA sequence (SEQ ID NO:5) of the CMV promoter of the expression cassette encoding the human thrombomodulin.

FIG. 7 is the cDNA (SEQ ID NO:6) of the human thrombomodulin gene.

DETAILED DESCRIPTION OF THE INVENTION

Figure 1:
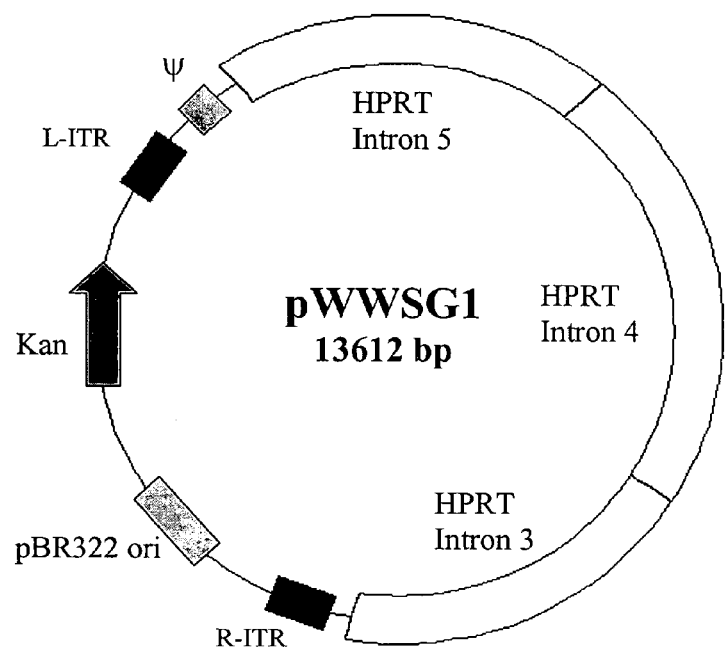
FIG. 1 is a schematic drawing of an embodiment of the backbone shuttle vector of the present invention.

The practice of the present invention will employ, unless other wise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The forth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HCl, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that are sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, (α-actin promoter and the like.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E. J., & Maniatis, T. (1989) Molecular Cloning: A Laboratory Manual (Cold Spring Harbor Lab. Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the—and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also include a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors:

The genome of an adenovirus can be manipulated such that it encodes and expresses a gene product of interest but is inactivated in terms of its ability to replicate in a normal lyric viral life cycle (Curie D T, Ann N Y Acad Sci 886, 158–171 [1991]). Suitable adenoidal vectors derived from the adenovirus strain Ad type 5d1324 or other strains of adenovirus (e.g., Ad2, Ad3, Ad7 etc.) are well known to those skilled in the art. Recombinant adenovirus es are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases relative to other gene delivery vectors (Haj-Ahmand et al. J. Virol. 57, 267–273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (U.S. Pat. No. 5,985,846 and U.S. Pat. No. 6,083,750).

Adenovirus vectors have been successfully tested in a number of animal models (Ragot et al. Nature 361, 647–650 [1993]; Howell et al. Hum Gene Ther 9, 629–634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1–5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944–8960 (1996).

The "inverted terminal repeats (ITRs) of adenovirus" are short elements located at the 5' and 3' termini of the linear adenoviral genome, respectively and are required for replication of the viral DNA. The left ITR is located between 1–130 bp in the Ad genome (also referred to as 0–0.5 mu). The right ITR is located from about 3,7500 bp to the end of the genome (also referred to as 99.5–100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the ψ sequence which comprises five (AI–AV) packaging signals and is required for encapsidation of the mature linear genome; the packaging signals are located from about 194 to 358 bp in the Ad genome (about 0.5–1.0 mu).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 Kb. (FIG. 1 and SEQ ID NO:1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO:1, preferably comprises at least 90 contiguous bases of SEQ ID NO:1, more preferably comprises at least 300 contiguous bases of SEQ ID NO:1, and most preferably comprises 3000 or more contiguous bases of SEQ ID NO:1.

The present invention also relates to a gutless adenoviral vector that carries the a DNA sequence encoding a native TM protein or a variant of a TM protein. In one embodiment, the DNA sequence is controlled by a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP 16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547–5551, [1992]; Gossen et al., *Science* 268: 1766–1769, [1995]; Kistner et al., *PNAS USA* 93: 10933–10938, [1996]).

Ecdysone system. The Ecdysone system is based on the molting induction system found in Drosophila, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346–3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180–8184, [1994]; Wang et al., *Nat. Biotech* 15: 239–243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been J. "used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865–2872, [1997]; Ye et al., *Science* 283:88–91, [1999]).

Ex Vivo and in Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ BD NO:3) have been reported (Suzuki et al. *EMBO J.* 6:1891–1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

EXAMPLE 1

Construction of Gutless Viral Backbone Shuttle Vector

An embodiment of a gutless viral backbone shuttle vector pShuttle is shown in FIG. 1. Sequence portion containing R-ITR, PBR322 ori, Kan, L-ITR, and encapsidation signal was obtained from the pAdEasy® system from STRATAGENE®. At bp 3667 of the original pShuttle sequence, there is a BamHI site just beyond the R-ITR. PCR primers were designed to include the BamHI site and then was to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

Insertion of the HPRT introns was a two step cloning process. First, the viral backbone was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence.

EXAMPLE 2

Construction and Preparation of Gutless Viral Shuttle Vector (a). Construction and Preparation of Gutless Viral Shuttle Vector Carrying Human Thrombomodulin Gene The insertion of hTM into the gutless adenovirus backbone first required the creation of a CMV-HTM expression cassette.

The intermediate vector used was pcDNA3.1I/Zeo(+) (Invitrogen). A CMV promoter is available commercially and a CMV promoter was cloned into the multiple cloning site (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (FIG. 6, SEQ ID NO:5) was inserted in a backwards orientation relative to the pcDNA3.1/Zeo(+) plasmid. The TM cDNA (FIG. 7, SEQ ID NO:6) was obtained from Dr. Sadler (Dittman et al., *Biochemistry*, 26(14):4350–4357 [1987]) which the sequence was submitted to ATCC and to GenBank. The TM gene was removed from the plasmid using EcoRI and inserted into pcDNA3.1/Zeo(+), also in the reverse orientation to pcDNA3.1/Zeo(+) downstream of the inserted CMV promoter. To remove the cassette, PmeI enzyme was used to cut both ends of the MCS. The gutless adenovirus backbone was linearized using SmaI which is at bp 381 of the backbone. The two were ligated together in the forwards orientation with respect to the gutless virus backbone. Sequence of the expression cassette (from PmeI site to PmeI site, SEQ ID NO:4) is shown in FIG. 5.

(b). Construction and Preparation of Gutless Viral Shuttle Vector Carrying LacZ Gene The insertion of LacZ also required creation of an intermediate vector to create the expression cassette. pcDNA3.1/Zeo(+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus

The helper virus is an E1/E3 deleted adenovirus in which a special flp recognition sequence site (FRS) flanks the encapsidation signal. Helper adenovirus need to be grown in 293 cells.

293 cell line has long ago been engineered to express E1 and E3 genes of adenovirus. These two genes are necessary for viral reproduction. The flp gene is similar in function to Cre-Lox. The flp gene will recognize the FRS, cleave at that location, and then relegate the DNA. It's basic function is to promote recombination between different pieces of DNA with the FRS, but in this case, it will cleave out the encapsidation signal thereby not allowing helper-viral DNA to be packaged. (Beauchamp et al., *Molecular Therapy*, 3(5):809–815 [2001]; Umana et al., *Nature Biotechnology*, 19:582–585 [2001])

293-flp cells will be transfected with the backbone DNA using Lipofectamine. While performing the transfection, helper virus were also used to infect the 293-flp cells. The helper virus were inserted its own DNA into the 293-flp cells. The flp protein expressed in the cells will cleave the encapsidation signal thereby not allowing the helper virus DNA to package. Consequently the gutless adenovirus backbone DNA was packaged into the adenoviral proteins expressed from the helper virus DNA. This virus will not be able to replicate in normal cells due to the E1/E3 deletions and will also contain the TM expression cassette.

The virus were produced by the following procedure:

(a) Virus Reproduction

Seed 293 cells in 15 cm dishes and grow in 10% FBS until approximately 70% confluent. Viral media was made as follows. 2 mL of FBS-free IMEM containing antibiotic, antimycotic; adjust pfu per cell of purified virus until reached the final concentration of media as 1 µl virus in 2 ml IMEM (viral Conc. 1×10$^{10}$ pfu/mL)/each 15 cm Dish. For Example: 30 Dishes=60 mL IMEM+30 µl virus Old media was Aspirated from dishes, and 2 ml viral media was added per dish. Dishes were rocked at 37° C. for 1.5–2 hours, and 18 mL 10% media was added per dish and incubated according to time course.

Cells were harvested by pipeting and collocating in 50 mL tubes at 4° C., and cells were centrifuge at 4° C., 2000 rpm for 5 min. Save 10 mL of supernatant from one of the tubes into a separate tube. The supernatant was removed from all of the tubes. Take 5 mL supernatant from the saved tube and resuspend all the pellets to one tube. All of the tubes were re-wash with the remaining 5 mL of supernatant to collect any leftover sample, and the pellet was store at −80° C.

(b) Virus Collection

Sample tube(s) were frozen/thawed 5 times to lyse the cells, and the virus were released using dry ice and incubated at 37° C. water bath for 15 minutes until each to obtain crude viral lysate (CVL). The CVL was collected in two 2059 Falcon Tubes and centrifuged using Sorvall HS4 at 7000 rpm, 4° C. for 5 minutes and the supernatant was recovered.

To purify the virus, ultra-clear SW41 (Beckman) tubes were prepared by soaking in Ultra Pure Water, then 70% ETOH. Cotton swabs (one swab for each tube) was used to completely dry out the tube, and two tubes were used per sample.

Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10×Dialysis Buffer: 100 mM Tris—pH 7.4, 10 mM MgCl$_2$; (2) 1×Dialysis Buffer (2 Liters): 400 mL Glycerol, 200 mL 10×Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 µg/ml. (BSA is fine). Sample cuvettes were prepared using 1–10 µl of sample, depending on estimate of titer. (Sample OD must be within the linear range of the standard line.) OD was taken at 595λ and formula of the line was calculate from standards. The protein concentration of the samples were calculated using this formula. The following formula was used to convert protein concentration to titer: [12.956+224.15 (µg/ml)]×10$^8$.

EXAMPLE 4

Expression of Human Thrombomodulin (hTM) in Vitro

When enough hTM gutless adenovirus has been produced, experiments will be performed to demonstrate the viable expression of hTM in HUVEC cells post infection with the hTM containing gutless adenovirus. To detect hTM expression post infection of HUVEC cells, RT-PCR will be performed using hTM specialized primers to detect for thrombomodulin mRNA. Also, western blots will be performed to detect hTM protein expression by the HUVEC cells.

As a control, the same HUVEC cells will be infected the gutless adenovirus expressing LacZ. These cells will subsequently be stained with X-gal to look for blue cells. This will demonstrate the viability of the gutless adenovirus backbone itself.

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an acellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240), and. The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for treating a vascular disease in a mammal, wherein said method comprising the steps of:
   infecting a seament of a blood vessel in vitro using a gutless adenoviral vector which comprises a polynucleotide encoding a thrombomodulin protein having the amino acid sequence of SEQ ID NO:2 and a regulatory element operably linked to said polynucleotide sequence;
   grafting the virus-treated blood vessel in said mammal, wherein said thrombomodulin protein is expressed in said virus-treated blood vessel in an amount sufficient to reduce re-occlusion or intimal hyperplasia in the grafted blood vessel.

2. The method of claim 1, wherein the regulatory element is a constitutive promoter selected from a group consisting of CMV promoter and RSV promoter.

3. The method of claim 1, wherein the expression of said polynucleotide encoding a thrombomodulin protein is under the control of an inducible system.

4. The method of claim 1, wherein said gutless adenoviral vector is produced using a shuttle vector comprising a pBR322 replication origin, a selectable marker gene, an adenovirus left inverted terminal repeat, an adenovirus encapsidation signal, an intronic sequence, and an adenovirus right inverted terminal repeat.

5. The method of claim 4, wherein said selectable marker gene is Kanamycin resistance gene.

6. The method of claim 1, wherein said mammal is human.

7. The method of claim 1, wherein said infecting step further comprises:
   filling the blood vessel with a complete viral delivery system comprising of 1:1 mixture of Ham's F12 medium and DMEM, an effective amount of the gutless adenovirus vector, and an acellular oxygen carrier; and
   incubating the blood vessel with the complete viral delivery system for a desired period of time.

8. The method of claim 7, wherein said acellular oxygen carrier is selected from the group consisting of unmodified hemoglobin, chemically modified hemoglobin and perfluorochemical emulsions.

9. The method of claim 8, wherein said unmodified hemoglobin or chemically modified hemoglobin is used in the range of 3 g/dl to 10 g/dl.

10. The method of claim 7, wherein the complete viral delivery system further comprises at least one of L-glutamine, sodium bicarbonate, or antibiotic-antimycotic.

11. The method of claim 7, wherein the desired period of time is between 10 to 45 minutes.

12. The method of claim 7, wherein said acellular oxygen carrier is unmodified hemoglobin.

13. The method of claim 12, wherein said unmodified hemoglobin is present in an amount of 3 g/dl to 10 g/dl.

14. The method of claim 12, wherein the desired period of time is between 10 to 45 minutes.

* * * * *

SEQUENCE LISTING

```
<160> NUMBER OF SEQ ID NOS: 6

<210> SEQ ID NO 1
<211> LENGTH: 13600
<212> TYPE: DNA
<213> ORGANISM: Artificial Sequence
<220> FEATURE:
<223> OTHER INFORMATION: gutless backbone shuttle vector

<400> SEQUENCE: 1
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
```

-continued

```
taaatttggg cgtaaccgag taagatttgg ccattttcgc gggaaaactg aataagagga      300
agtgaaatct gaataatttt gtgttactca tagcgcgtaa tactggtacc gcggccgcct      360
cgagtctaga actagtggat cccccggctg caggaattct gatggctctc aaaattcctg      420
cctcctttag gggataaaag actttaagac tttttaacaa aaagaaaaa gaaaaaaaaa       480
attcctgcct cctggtgtac acacacagaa gggttccctc cccttgaatg tgaccaggat      540
ctgtgaaaat aacgggatag ccgctcctgt gattaggtta tgtggtagac tagagcaaga     600
ttctcctgct ggttttgaag aagtcagctg ccatgttgtg agactgtcat ggggctaggg      660
catgagcctt taaatatct gggagcaacc cctggccagc agccagtgag aaaacgggcc       720
ctcagtccta caatcacaag gaactaaatt ctgccaacaa cctgaaggaa ctttgaagag      780
gatcatgagt cccttgattc agcttgatga gcccctgagc agaggataca gctaacttgt      840
actagggaag tataaaaaac atgcatggga atgatatata tcaactttaa ggataattgt      900
catacttctg ggaatgaagg gaagaaatg gggctttagt tgtattatga tctttaattt       960
ctcaaaaaaa agatcagaag caaatatggc aaaatgttaa tacttttgtg ggtacgtagg     1020
tattcagcat acccttttt ctgagttcaa aatattttat aattaaaatg aaatgcaggc      1080
caggcacagt ggctcatgcc tataatacca gcactttgcg aggccgaggt gggaggatgg     1140
cttgaggcca gaccagcctg gccaacatgg caaaacccca tctctactta aaaaaaaaa     1200
aactatatat atatatatgt gtgtgtgtgt gtatatatat atatgtatat atatttatat    1260
atgtgtgtat atatatatat gtatatatat ttatatatgt gtgtgtatat atatatatac    1320
acacacacac atatatacat acatacatac acacacacac acacacaatt agccaggcat    1380
ggtggcgcac acctgtagtc ccagctactt gggaggctga gacatgagaa ttgcttgaac    1440
ctggggaggca gagtagttag tgagctgaga tcataccact gcactccagc ctggtgacag   1500
agtgagactc tgtcttaaaa aaaataaaaa ttaaaattaa atgcaaaagg tccaagtgaa    1560
ttgaagagga aaggggtatc aaggaaggtt ttgtggaggt gacgtttgag ctgggtctta    1620
aatgacttaa acatgggata agaagggagg gaataaggac atttcaggta cgagaaataa    1680
ggagcatcag tggaaacaac ctaacgtctg tcaaccagtg aatggataac aaaaatgtaa    1740
ttcagatggt atccaactta cgatggttcc aacatgagat ttttctgact ttaggataga    1800
tttatcaaag tagtaaatcc attttcaact tatgatattt tcaacttcag atgggtttat    1860
caggacacag ttgaggaaca cctgtctatc catacaattt ggcaataaaa aggaaatgag    1920
tgcagatata ctccacaaca tgaatgaacc ttgaaaacat taagtgagag aagccagata    1980
caaaaggcca catattgtat gattctattt atacaaaatg tccagaatag gcaaatctta    2040
tagacagcaa gtaggtagat gatcagtttg ctaggtgctg ggggaagggg aaatggggag    2100
tgatggctaa ggggattggg tttctttgtg gggaaatgaa atgttttaa aattgagcgt     2160
gataatgatt gctaatgctg catatatata taatctatag attatatata tataaagaga   2220
ggctgttaga cagtgataag tgatatatat atatatatac ataagagaga gagagagaga    2280
gagagagagg ctgttagtga taagtgatca ggaaaataaa agtattgagg aggaatacga    2340
agttgacggt gtgaaaacat gagattttat ataggatggc cagggaggcc ttaatgagaa    2400
agtgacttat gagtaaaaac aagggatcct aaaccttagc atgcatcaga atcactcgga    2460
aacttgttaa agcatagctt gctgggcctc atcacagata ttttgattcg gtaggttctt    2520
gtctgatatt aatactttg gtctagggaa ccacattttg agaaccactg agctaaagga     2580
```

```
agtaaaggtt tcccttagtt tactagctgg taaccctagg aaactgctta gcctctcggt   2640
gctaagatac aaaatacttt agcacataat aacacatgga aaatagtcta taaattataa   2700
atattatttt ttatgtacca aatattacat aagacaaaat ctaagcaagt atatatatat   2760
atacataaaa tataagatat atatgtatat attatatata gataaataga gagagagagt   2820
tatgtttaga agaaaatac ttcaaactaa aaaagagag gtaggaagta taccattcca     2880
ttattggtaa aaacaaatta ctaagtagtc tttacaaaaa acaatctcac tcctttagaa   2940
cacaagccca ccattaaaac tgatgcagag gaatttctct ccctggctta cctttaggat   3000
ggtgcatact aagttagaaa agtcataaat gttatattaa agtaaatgt gaacttactt    3060 ccacaatcaa gacattctag aagaaaaga gaaatgaaaa tcagtacaat gaataaaacg    3120
gtatttccaa ttataagtca aatcacatca taacaaccct aaggaattat ccaaactctt   3180
gtttttagat gctttattat atcaaactct ccttaaaca agtggcccat ctgctgggat    3240
ttggaagcct gtaatactga aattttcatc ataatgaaa ttttaaaaac agaattgacc    3300
cacctgtttt taaaacactt tcattactta acaagaggtc taatcttggg caagtcttga   3360
aatttctctg gccttagttt cccatgtgtt aaatgaaact tgaagcagtt ggtctcttat   3420
agtctcctga ctctaacatt ctaagaatta tatttgtaca ataactcaaa aatcacataa   3480
tttaatttac catatggact ccaaaatata ttttctcatt aggctaaact tgatctgcat   3540
tttctggatg tgtccatatt cttggactac actaaaacat gataccaatg cttcctctca   3600
ccataaaccc tcacttcgct ttctacattt aagaatttta tagctggaag agtccttaag   3660
agaaaatacc atctaataat taccccctcaa aatcgagaaa gtcctatctg ttcttatgct  3720
agttataaga atgaggcagc atttcacata atggttataa acactgccac aagaagattc   3780
atgatgtgtt gtttatctgt agctctcatc atactctgtc atataactat agcattaaga   3840
ttttaatgtt ctatatattc ttctaagaca gtgtttacca gagtaaggca caaaagatcc   3900
actggtttgc aagaaagatt agaactttta aatttttaa cctcaccttg tttaatctat    3960
atttttgtat gtatttgta acatatatat tattattacc ataaatcata tataatttaa   4020
aatgcatata ttaggggtaa atgctcagga aactttttat aaattgggca tgcaaataca   4080
agtttgaaga ctcactgttc taggtattaa agtaaagtt ataaccaagt aaagcttcca    4140 cctttttcatg tctcaaagca gtttattgtt ggaggtaaga tctcttagaa gcctaaacag  4200
gtccaagtac agaatgaagt aaggctagcc cataacttgt ggcaagcaat tcatactatt   4260
tctctcatgc tgagctctcc tcagtgaagc agctactata gacaactgca gcctattggt   4320
agcctatttt acaggcagga aaaaattac ttttttattc aaagtggaac tcaggacatg    4380
gggagaaaat gaatacaaaa aatagggtca atccaaaggc acacagcaaa tgagtaacac   4440
agttatgttt ttttcccatt tgtatgaggt cccagtaaat tctaagtaaa ctgcaaattt   4500
aataatacac taaaaaagcc atgcaattgt tcaaatgaat cccagcatgg tacaaggagt   4560
acagacacta gagtctaaaa aacaaagaa tgccattatt gagttttga attatatcaa     4620 gtagttacat ctctacttaa taaatgagaa aaacgaggat aagaggccat ttgataaaat   4680
gaaaatagcc aagaagtggt attagagact tgaatacagg tattcgggtc caaagttcat   4740
ctgctcaaat actaactggg gaaagaggg aaaatatttt atatacatat atatctgcac    4800 aaaaatacc ccaaaagaca aaatgaggcc aggcagggtg gctcacaccc gtaatcccgg    4860
tactttggga ggctgaggca ggtggatacc tgagatcagg agttggagat cagcctggtc   4920
aacatggtga aaccctgtct ctactaaaag ataaaaaat tagccaggca tggtggcgtg    4980
```

```
cgcctgtaat cccagctact tgggagtctg aggcaggaga atcacttgaa ctgggaaggg    5040
gaggttgcag tgagccaaga tcgtactact gcactccagc ctgggcagca gagtgagact    5100
ccatcacaaa ataaataaat aaataaaata caatgaaaca gaaagttcaa ataatcccat    5160
aatcttacca ccaagaaata actttcactc gttatactta ttgattttc cataataaat     5220 gtactttact gtgactatca tgaaaagaaa gttattttag aaacagagaa ctgtttcaga    5280
tcaaatctat gtagtagaac agagccatta ggtgggaaag acgagatcaa actaaatctc    5340
agaaggccta aaaggctagg tccattccag cactaaaaac tgaccagaca agtaatggct    5400
tcaacagctt ctaaatatgg acaaagcatg ctgaaaggga aggacaggtc taacagtggt    5460
atatgaaatg aacaggaggg gcaaagctca tttctcctct gaagttttcc aaagatgctg    5520
aggaggacat tagtttgaca tgaccctgat atgggacaag ataatttcac agaagtttta    5580
catgttaaag ttttcttata gatactcatt caagtaagca atgaacacta aaatctaaag    5640
aaagaaaaga gctttagagt caggtctgta ttcaaattca agctctacca cttactggtt    5700
ctgtgacttt gggcaagtct tttacccta ttaagtctta atttcctgat ttgtaaaatg     5760
gggatatcgt ctccctcaca ggattgttgt gaaacttta tgagattaat gcctttatat     5820
ttggcatagt gtaagtaaac aataactggc agcttcaaaa aaaaaagca gtagcattcc     5880 atcatttatt attggttact ctcaaaaagt ttttcaatgt actagaagat aaatattcaa    5940
ataccttaat atctccatta ttttcaggta aacagcatgc tcctgaacaa ccaatgggtc    6000
aacaaataaa ttaaaaggga atctaaaaa catcttgata ttaaactaca tggaagcaca    6060
atataccaaa accatggttc acactaggag aattttaagg tacaagaaaa ctctttgaga    6120
tttcttaaaa taatagtatg tctgaattta ttgagtgatt taccagaaac tgttgtaaga    6180
gctctacttg cattatagca cttaatcctc ttaactctat ggctgctatt atcaacctca    6240
ccctaatcac atatgggaca cagagaggtt aagtaacttg cccaaggtca gagttaggaa    6300
gtactaagcc atgctttgaa tcagttgtca ggctccggaa ctcacacttt cagccactac    6360
ataatactgc tttgctatct tttaggaaac tatgtgagtc tacctcacat agactcacat    6420
aggtttgttt tttttttttt tttaaaggct atcttttccc ccatcaatgt tttttgaagg    6480
atcccaaatt agagtcccac agaggcagac agcagtactt gacaatatgg acatttaagg    6540
ttaatgttgg attctactgt ctttttacta catgacctag ggaacgataa ttaacctaga    6600
ctgcttccaa gggttaaata acccatttag ttatactatg taaattatct cttagtgatt    6660
gattgaaagc acactgttac taattgactc ggtatgaagt gctttttttt cttcccttc     6720 aagatacata cctttccagt taaagttgag agatcatctc caccaattac ttttatgtcc    6780
cctgttgact ggtcattcta gttaaaaaaa aaaaactat atatatatat atctacacac     6840
acatatgtat atgtatatcc ttatgtacac acacaaactt caaattaaat gagaactaga    6900
agatttgaga agttagctag ctaatatcca tagcattatg atattctaaa tgatatgaat    6960
tataagaatt aggtttcctg aaatgaatga ctagaaaact ttcaagtaga gattagtaaa    7020
aattaaaaag tcctaatcgg ccattactga tttgatgttt ttaagagtcc taaaaaatgg    7080
gttacatcca tttttaagtg ggtagtatta aacagccac ccatcttcaa tcacagtgat      7140
ttctgaattg tgagggaagt tattagcatg acaggtgtct ggttctggcc ctgtacgatt    7200
cccatgagtc aagcaaattg taagggctgg tctatatcac acccaacccc aaggatatgt    7260
ccctcaaaag tctagcccag gccccgtcat cttcagcatc atctgggaaa ccaggtctga    7320
```

```
ttagtagtcc tttaaggata cctcttaggc tcccatttta ctgctatcac agaatccaat    7380
aaaacccttA caggagattc aatgggaaat gctcaacacc cactgtagtt ggtggtgaca    7440
atgaccataa tttggctgtg ctggattcag gacagaaaat ttgggtgaaa gagcaggtga    7500
acaaagagc ttcgacttgc cctagcagag agcaagccat accataccac aaagccacag     7560
aattacaacg gtgcagtacc agcacagtaa atgaacaaag tagagcccag aaacagaccc    7620
agaactatat gaggatttag tatacaataa agatggtatt tcgagtcagt agggaaaaga   7680
tgaattattc aataaatgat gtttggccaa ctagtaaccc atttgggaaa aataaaagt     7740
atggtcccta cctcacagca tacacaaaaa taaattccag acggattaaa atctaaatgt    7800
aaaaaataaa gccataagtg gactggaaga aaatagagaa ttttttttaa catccgtaga    7860
aagggtaaaa acccaggcat gacatgaacc aaaactgaag aggttctgta acaaatccc     7920
ccttttatat attgggctcc aacaataaga acccatagga aaatggagaa tgaacacaaa    7980
tagacaattt atagaagaga aggttataag gtgtaaaatt atatctatct gagaaacaaa    8040
cactaaaaca atgtgattct actgttctcc cacccatact ggcaaaactt aagcctgata    8100
atatgctgag gggaaataag cactcttgtt ggtgagagta ttaattggca tagcttcttt    8160
tgaaaatgac atagcaatac ctgttaaaat tgcaaacatg catgtcactt aattccatgt    8220
aattcccact tctgggaatc aattgctaca aaaacacttg acaagtatac aaagatacat    8280
tcaagagtgt tcactgggcc gggtgcggtg gcttcatgcc tgtaatccca gggaggcaga    8340
ggcaagacga tcgcttgacc ccaggagttc aaggccagcc cgagaaacac agcaagaccc    8400
tgtctctctt ttttttattt aaaaaataaa tgttcactgt atcagttgtt cacaaaaaca    8460
aaccaacatg tccattaaca gggaaccatt taaattaatc aagttcatct acacaatgta    8520
ataccatgca actattaaaa agcacctgat aatccaaagc acactgagac agaataatgc    8580
tattaaaaac accaagtagt ggaacactgt gttgcctatg acaccatttt tattcaacat    8640
ttaaacaaat ttgtaacagc aattacatga gtagtgacaa tggcgtttat gagacttttc    8700
acttttatgt gcttctatttt ttgttatgct tctatatata catccatttta ttatggagtg   8760
ttactttcaa aaatcacaaa tgggccagta ttatttggtg ttgcaaggtg agcatatgac    8820
ttctgatatc aacctttgca tattacttct caatttaggg aaattacaga catcccttat    8880
tctaactaac ttaaaaccca gcatttcaaa catacagaat tgatggggaa aaaaagaaag   8940
aagaaagaaa gaaaaggcaa caagcttcag atgacagtga ctcacatcaa attatttata    9000
aaatctgtta aatagtgcca tcttctggag atacctggta ttacagtcca actccagttg    9060
atgtctttac agagacaaga ggaataaagg aaaaaatatt caagaactga aaagtatgga    9120
gtcatggaaa aattgctgtg atccaaaggc tacggtgata ggacaagaaa caagagaact    9180
ccaagcagta agacactgct gttctattag catccaaacc tccataccctc ctgtttgccc   9240
caaggctttt ttaaaaaata gagacaggat ctcactattt tgctcaggct ggtcttgaac    9300
tcctggactc aagctatcct cctgcctcgg cctcctaaag tgccgagatt acaggcttga    9360
gtcaccatac ctggctattt attttttctt aactctcttg cctggcctat agccaccatg    9420
gaagctaata aagaatatta atttaagagt aatggtatag ttcactacat tggaatacag    9480
gtataagtgc ctacattgta catgaatggc atacatggat caattacccc acctgggtgg    9540
ccaaaggaac tgcgcgaacc tccctccttg gctgtctgga acaagcttcc cactagatcc    9600
ctttactgag tgcctccctc atctttaatt atggttaagt ctaggataac aggactggca    9660
aaggtgaggg gaaagcttcc tccagagttg ctctaccctc tcctctaccg tcctattctc    9720
```

```
ctcactcctc tcagccaagg agtccaatct gtcctgaact cagagcgtca ctgtcaacta    9780
catcaaaatt gccagagaag ctctttggga ctacaaacac ataccettaa tgtctttatt    9840 tctattttgt ctacctcttc agtctaggtg aaaaaatagg aaggataata gggaagaact    9900
ttgtttatgc ctacttatcc gccctaggaa attttgaaaa cctctaggta gcaataagaa    9960
ctgcagcatg gtatagaaaa agaggaggaa agctgtatag aaatgcataa taaatgggca   10020
ggaaaagaac tgcttggaac aaacagggag gttgaactat aaggagagaa agcagagagg   10080
ctaatcaaca aggctgggtt cccaagaggg catgatgaga ctattactaa ggtaggaatt   10140
actaagggct tccatgtccc cttagtggct tagtactatg tagcttgctt tctgcagtga   10200
acttcagacc cttcttttag gatcctagaa tggactttt tttttatcg gaaacagtc    10260 attctctcaa cattcaagca ggccccaagt ctaccacact caatcacatt ttctcttcat   10320
atcataatct ctcaaccatt ctctgtcctt ttaactgttt ttctataccc tgatcaaatg   10380
ccaacaaaaa gtgagaatgt tagaatcatg tatttttaga ggtagactgt atctcagata   10440
aaaaaaaagg ggcagatatt ccattttcca aaatatgtat gcagaaaaaa taagtatgaa   10500
aggacatatg ctcaggtaac aagttaattt gtttacttgt attttatgaa ttccctaaaa   10560
cctacgtcac ccgccccgtt cccacgcccc gcgccacgtc acaaactcca ccccctcatt   10620
atcatattgg cttcaatcca aaataaggta tattattgat gatgttaatt aacatgcatg   10680
gatccatatg cggtgtgaaa ataccgcaca gatgcgtaag gagaaaatac cgcatcaggc   10740
gctcttccgc ttcctcgctc actgactcgc tgcgctcggt cgttcggctg cggcgagcgg   10800
tatcagctca ctcaaaggcg gtaatacggt tatccacaga atcaggggat aacgcaggaa   10860
agaacatgtg agcaaaaggc cagcaaaagg ccaggaaccg taaaaaggcc gcgttgctgg   10920
cgttttccca taggctccgc cccctgacg agcatcacaa aaatcgacgc tcaagtcaga   10980
ggtggcgaaa cccgacagga ctataaagat accaggcgtt tccccctgga agctccctcg   11040
tgcgctctcc tgttccgacc ctgccgctta ccggatacct gtccgccttt ctcccttcgg   11100
gaagcgtggc gctttctcat agctcacgct gtaggtatct cagttcggtg taggtcgttc   11160
gctccaagct gggctgtgtg cacgaacccc ccgttcagcc cgaccgctgc gccttatccg   11220
gtaactattc gtcttgagtc aacccggta agacacgact tatcgccact ggcagcagcc   11280
actggtaaca ggattagcag agcgaggtat gtaggcggtg ctacagagtt cttgaagtgg   11340
tggcctaact acggctacac tagaaggaca gtatttggta tctgcgctct gctgaagcca   11400
gttaccttcg gaaaaagagt tggtagctct tgatccggca acaaaccac cgctggtagc    11460 ggtggttttt ttgtttgcaa gcagcagatt acgcgcagaa aaaaggatc tcaagaagat    11520 cctttgatct tttctacggg gtctgacgct cagtggaacg aaaactcacg ttaagggatt   11580
ttggtcatga gattatcaaa aaggatcttc acctagatcc ttttaaatta aaatgaagt   11640 tttaaatcaa tctaaagtat atatgagtaa acttggtctg acagttacca atgcttaatc   11700
agtgaggcac ctatctcagc gatctgtcta tttcgttcat ccatagttgc ctgactcccc   11760
gtcgtgtaga taactacgat acgggagggc ttaccatctg gccccagtgc tgcaatgata   11820
ccgcgagacc cacgctcacc ggctccagat ttatcagcaa taaccagcc agccggaagg   11880 gccgagcgca gaagtggtcc tgcaacttta tccgcctcca tccagtctat taattgttgc   11940
cgggaagcta gagtaagtag ttcgccagtt aatagtttgc gcaacgttgt tgccattgct   12000
gcagccatga gattatcaaa aaggatcttc acctagatcc ttttcacgta gaaagccagt   12060
```

-continued

```
ccgcagaaac ggtgctgacc ccggatgaat gtcagctact gggctatctg dacaagggaa      12120
aacgcaagcg caaagagaaa gcaggtagct tgcagtgggc ttacatggcg atagctagac      12180
tgggcggttt tatggacagc aagcgaaccg gaattgccag ctgggccct ctggtaaggt       12240
tgggaagccc tgcaaagtaa actggatggc tttcttgccg ccaaggatct gatggcgcag     12300
gggatcaagc tctgatcaag agacaggatg aggatcgttt cgcatgattg aacaagatgg     12360
attgcacgca ggttctccgg ccgcttgggt ggagaggcta ttcggctatg actgggcaca     12420
acagacaatc ggctgctctg atgccgccgt gttccggctg tcagcgcagg ggcgcccggt     12480
tcttttgtc aagaccgacc tgtccggtgc cctgaatgaa ctgcaagacg aggcagcgcg      12540
gctatcgtgg ctggccacga cgggcgttcc ttgcgcagct gtgctcgacg ttgtcactga    12600
agcgggaagg gactggctgc tattgggcga agtgccgggg caggatctcc tgtcatctca     12660
ccttgctcct gccgagaaag tatccatcat ggctgatgca atgcggcggc tgcatacgct    12720
tgatccggct acctgcccat tcgaccacca agcgaaacat cgcatcgagc gagcacgtac    12780
tcggatggaa gccggtcttg tcgatcagga tgatctggac gaagagcatc aggggctcgc    12840
gccagccgaa ctgttcgcca ggctcaaggc gagcatgccc gacggcgagg atctcgtcgt    12900
gacccatggc gatgcctgct tgccgaatat catggtggaa aatggcgctt tctggattc    12960
atcgactgtg gccggctggg tgtggcggac cgctatcagg acatagcgtt ggctacccgt   13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccat aggccgaaat cggcaaaatc    13200
ccttataaat caaagaaata gaccgagata gggttgagtg ttgttccagt ttggaacaag    13260
agtccactat taaagaacgt ggactccaac gtcaaagggc gaaaaaccgt ctatcagggc    13320
gatggcccac tacgtgaacc atcaccctaa tcaagttttt tggggtcgag gtgccgtaag    13380
cactaaatcg gaaccctaaa gggagccccc gatttagagc ttgacgggga agccggcga     13440
acgtggcgag aaaggaaggg aagaaagcga aaggagcggg cgctagggcg ctggcaagtg    13500
tagcggtcac gctgcgcgta accaccacac ccgccgcgct taatgcgccg ctacagggcg    13560
cgtccattcg ccattcagga tcgaattaat tcttaattaa                          13600
```

<210> SEQ ID NO 2
<211> LENGTH: 574
<212> TYPE: PRT
<213> ORGANISM: Homo sapien

<400> SEQUENCE: 2

```
Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
    65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
```

-continued

```
                100                 105                 110
Gly Asp Asn Asn Thr Ser Tyr Ser Arg Trp Ala Arg Leu Asp Leu Asn
            115                 120                 125
Gly Ala Pro Leu Cys Gly Pro Leu Cys Val Ala Val Ser Ala Ala Glu
130                 135                 140
Ala Thr Val Pro Ser Glu Pro Ile Trp Glu Glu Gln Gln Cys Glu Val
145                 150                 155                 160
Lys Ala Asp Gly Phe Leu Cys Glu Phe His Phe Pro Ala Thr Cys Arg
                165                 170                 175
Pro Leu Ala Val Glu Pro Gly Ala Ala Ala Ala Val Ser Ile Thr
            180                 185                 190
Tyr Gly Thr Pro Phe Ala Ala Arg Gly Ala Asp Phe Gln Ala Leu Pro
        195                 200                 205
Val Gly Ser Ser Ala Ala Val Ala Pro Leu Gly Leu Gln Leu Met Cys
    210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Gly Cys Glu His Ala Cys
                245                 250                 255
Asn Ala Ile Pro Gly Ala Arg Pro Cys Gln Cys Pro Ala Gly Ala Ala
            260                 265                 270
Leu Gln Ala Asp Gly Arg Ser Cys Thr Ala Ser Thr Gln Ser Cys Asn
        275                 280                 285
Asp Leu Cys Glu His Phe Cys Val Pro Asn Pro Asp Gln Pro Gly Ser
    290                 295                 300
Tyr Ser Cys Met Cys Glu Thr Gly Tyr Arg Leu Ala Ala Asp Gln His
305                 310                 315                 320
Arg Cys Glu Asp Val Asp Asp Cys Ile Leu Glu Pro Ser Pro Cys Pro
                325                 330                 335
Gln Arg Cys Val Asn Thr Gln Gly Gly Phe Glu Cys His Cys Tyr Pro
            340                 345                 350
Asn Tyr Asp Leu Val Asp Gly Glu Cys Val Glu Pro Val Asp Pro Cys
        355                 360                 365
Phe Arg Ala Asn Cys Glu Tyr Gln Cys Gln Pro Leu Asn Gln Thr Ser
    370                 375                 380
Tyr Leu Cys Val Cys Ala Glu Gly Phe Ala Pro Ile Pro His Glu Pro
385                 390                 395                 400
His Arg Cys Gln Met Phe Cys Asn Gln Thr Ala Cys Pro Ala Asp Cys
                405                 410                 415
Asp Pro Asn Thr Gln Ala Ser Cys Glu Cys Pro Glu Gly Tyr Ile Leu
            420                 425                 430
Asp Asp Gly Phe Ile Cys Thr Asp Ile Asp Glu Cys Glu Asn Gly Gly
        435                 440                 445
Phe Cys Ser Gly Val Cys His Asn Leu Pro Gly Thr Phe Glu Cys Ile
    450                 455                 460
Cys Gly Pro Asp Ser Ala Leu Ala Arg His Ile Gly Thr Asp Cys Asp
465                 470                 475                 480
Ser Gly Lys Val Asp Gly Gly Asp Ser Gly Ser Gly Glu Pro Pro Pro
                485                 490                 495
Ser Pro Thr Pro Gly Ser Thr Leu Thr Pro Pro Ala Val Gly Leu Val
            500                 505                 510
His Ser Gly Leu Leu Ile Gly Ile Ser Ile Ala Ser Leu Cys Leu Val
        515                 520                 525
```

Val Ala Leu Leu Ala Leu Leu Cys His Leu Arg Lys Lys Gln Gly Ala
    530                 535                 540

Ala Arg Ala Lys Met Glu Tyr Lys Cys Ala Ala Pro Ser Lys Glu Val
545                 550                 555                 560

Val Leu Gln His Val Arg Thr Glu Arg Thr Pro Gln Arg Leu
            565                 570

<210> SEQ ID NO 3
<211> LENGTH: 1725
<212> TYPE: DNA
<213> ORGANISM: Homo sapien

<400> SEQUENCE: 3

| | | | | | |
|---|---|---|---|---|---|
| atgcttgggg | tcctggtcct | tggcgcgctg | gccctggccg | gcctggggtt | ccccgcaccc | 60 |
| gcagagccgc | agccgggtgg | cagccagtgc | gtcgagcacg | actgcttcgc | gctctacccg | 120 |
| ggccccgcga | ccttcctcaa | tgccagtcag | atctgcgacg | gactgcgggg | ccacctaatg | 180 |
| acagtgcgct | cctcggtggc | tgccgatgtc | atttccttgc | tactgaacgg | cgacggcggc | 240 |
| gttggccgcc | ggcgcctctg | gatcggcctg | cagctgccac | ccggctgcgg | cgaccccaag | 300 |
| cgcctcgggc | ccctgcgcgg | cttccagtgg | gttacgggag | acaacaacac | cagctatagc | 360 |
| aggtgggcac | ggctcgacct | caatggggct | cccctctgcg | gcccgttgtg | cgtcgctgtc | 420 |
| tccgctgctg | aggccactgt | gcccagcgag | ccgatctggg | aggagcagca | gtgcgaagtg | 480 |
| aaggccgatg | gcttcctctg | cgagttccac | ttcccagcca | cctgcaggcc | actggctgtg | 540 |
| gagcccggcg | ccgcggctgc | cgccgtctcg | atcacctacg | caccccgtt | cgcggcccgc | 600 |
| ggagcggact | ccaggcgct | gccggtgggc | agctccgccg | cggtggctcc | cctcggctta | 660 |
| cagctaatgt | gcaccgcgcc | gcccggagcg | gtccagggc | actgggccag | ggaggcgccg | 720 |
| ggcgcttggg | actgcagcgt | ggagaacggc | ggctgcgagc | acgcgtgcaa | tgcgatccct | 780 |
| ggggctcccc | gctgccagtg | cccagccggc | gccgccctgc | aggcagacgg | cgcgctcctgc | 840 |
| accgcatccg | cgacgcagtc | ctgcaacgac | ctctgcgagc | acttctgcgt | tcccaacccc | 900 |
| gaccagccgg | gctcctactc | gtgcatgtgc | gagaccggct | accggctggc | ggccgaccaa | 960 |
| caccggtgcg | aggacgtgga | tgactgcata | ctggagccca | gtccgtgtcc | gcagcgctgt | 1020 |
| gtcaacacac | agggtggctt | cgagtgccac | tgctaccctc | actacgacct | ggtggacggc | 1080 |
| gagtgtgtgg | agcccgtgga | cccgtgcttc | agagccaact | gcgagtacca | gtgccagccc | 1140 |
| ctgaaccaaa | ctagctacct | ctgcgtctgc | gccgagggct | tcgcgcccat | tccccacgag | 1200 |
| ccgcacaggt | gccagatgtt | ttgcaaccag | actgcctgtc | cagccgactg | cgaccccaac | 1260 |
| acccaggcta | gctgtgagtg | ccctgaaggc | tacatcctgg | acgacggttt | catctgcacg | 1320 |
| gacatcgacg | agtgcgaaaa | cggcggcttc | tgctccgggg | tgtgccacaa | cctccccggt | 1380 |
| accttcgagt | gcatctgcgg | gcccgactcg | gcccttgccc | gccacattgg | caccgactgt | 1440 |
| gactccggca | aggtggacgg | tggcgacagc | ggctctggcg | agccccgcc | cagcccgacg | 1500 |
| cccggctcca | ccttgactcc | tccggccgtg | gggctcgtgc | attcgggctt | gctcataggc | 1560 |
| atctccatcg | cgagcctgtg | cctggtggtg | gcgcttttgg | cgctcctctg | ccacctgcgc | 1620 |
| aagaagcagg | gcgccgccag | ggccaagatg | gagtacaagt | gcgcggcccc | ttccaaggag | 1680 |
| gtagtgctgc | agcacgtgcg | gaccgagcgg | acgccgcaga | gactc | | 1725 |

<210> SEQ ID NO 4
<211> LENGTH: 4454

```
<212> TYPE: DNA
<213> ORGANISM: Homo sapien
<220> FEATURE:
<221> NAME/KEY: misc_feature
<222> LOCATION: 349
<223> OTHER INFORMATION: n = A,T,C or G

<400> SEQUENCE: 4
```

| | | | | |
|---|---|---|---|---|
| gtttaaacgg | gccctctaga | cgcgttgaca | ttgattattg | actagttatt aatagtaatc | 60 |
| aattacgggg | tcattagttc | atagcccatg | atatcatatg | gagttccgcg ttacataact | 120 |
| tacggtaaat | ggcccgcctg | gctgaccgcc | caacgacccc | cgcccattga cgtcaataat | 180 |
| gacgtatgtt | cccatagtaa | cgccaatagg | gactttccat | tgacgtcaat gggtggagta | 240 |
| tttacggtaa | actgcccact | tggcagtaca | tcaagtgtat | catatgccaa gtacgccccc | 300 |
| ctattgacgt | caatgacggt | aaatggcccg | cctggcatta | tgcccagtnc atgaccttat | 360 |
| gggactttcc | tacttggcag | acatctacgt | attagtcatc | gctattacca tggtgatgcg | 420 |
| gttttggcag | tacatcaatg | ggcgtggata | gcggtttgac | tcacggggat tttccaagtc | 480 |
| tccaccccat | tgacgtcaat | gggagtttgt | tttggcacca | aaatcaacgg gactttccaa | 540 |
| aatgtcgtaa | caactccgcc | ccattgacgc | aaatgggcgg | taggcgtgta cggtgggagg | 600 |
| tctatataag | cagagctctc | tggctaacta | gagaacccct | gcttactggc ttatcgagat | 660 |
| atctgcagaa | ttcatctgtc | gactgctacc | ggcagcgcg | agcggcaaga agtgtctggg | 720 |
| ctgggacgga | caggagaggc | tgtcgccatc | ggcgtcctgt | gccctctgc tccggcacgg | 780 |
| ccctgtcgca | gtgcccgcgc | tttccccggc | gcctgcacgc | ggcgcgcctg gtaacatgc | 840 |
| ttggggtcct | ggtccttggc | gcgctggccc | tggccggcct | ggggttcccc gcacccgcag | 900 |
| agccgcagcc | gggtggcagc | cagtgcgtcg | agcacgactg | cttcgcgctc tacccggggcc | 960 |
| ccgcgacctt | cctcaatgcc | agtcagatct | gcgacggact | gcggggccac ctaatgacag | 1020 |
| tgcgctcctc | ggtggctgcc | gatgtcattt | ccttgctact | gaacggcgac ggcggcgttg | 1080 |
| gccgccggcg | cctctggatc | ggcctgcagc | tgccacccgg | ctgcggcgac cccaagcgcc | 1140 |
| tcgggcccct | cgcgcggcttc | cagtgggtta | cgggagacaa | caacaccagc tatagcaggt | 1200 |
| gggcacggct | cgacctcaat | ggggctcccc | tctgcggccc | gttgtgcgtc gctgtctccg | 1260 |
| ctgctgaggc | cactgtgccc | agcgagccga | tctgggagga | gcagcagtgc gaagtgaagg | 1320 |
| ccgatggctt | cctctgcgag | ttccacttcc | agccacctg | caggccactg gctgtggagc | 1380 |
| ccggcgccgc | ggctgccgcc | gtctcgatca | cctacgcac | cccgttcgcg gcccgcggag | 1440 |
| cggacttcca | ggcgctgccg | gtgggcagct | ccgccgcggt | ggctcccctc ggcttacagc | 1500 |
| taatgtgcac | cgcgccgccc | ggagcggtcc | aggggcactg | ggccagggag cgccggggcg | 1560 |
| cttgggactg | cagcgtggag | aacggcggct | gcgagcacgc | gtgcaatgcg atccctgggg | 1620 |
| ctccccgctg | ccagtgccca | gccggcgcgcc | cctgcaggc | agacgggcgc tcctgcaccg | 1680 |
| catccgcgac | gcagtcctgc | aacgacctct | gcgagcactt | ctgcgttccc aaccccgacc | 1740 |
| agccgggctc | ctactcgtgc | atgtgcgaga | ccggctaccg | gctggcggcc gaccaacacc | 1800 |
| ggtgcgagga | cgtggatgac | tgcatactgg | agcccagtcc | gtgtccgcag cgctgtgtca | 1860 |
| acacacaggg | tggcttcgag | tgccactgct | accctaacta | cgacctggtg gacggcgagt | 1920 |
| gtgtggagcc | cgtggacccg | tgcttcagag | ccaactgcga | gtaccagtgc cagccctga | 1980 |
| accaaactag | ctacctctgc | gtctgcgcc | agggcttcgc | gcccattccc acgagccgc | 2040 |
| acaggtgcca | gatgttttgc | aaccagactg | cctgtccagc | cgactgcgac cccaacaccc | 2100 |

```
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcacccca gctttgctac caaagcacct     2640
tagctggcat tacagctgga gaagaccctc cccgcacccc caagctgttt tcttctattc    2700
catggctaac tggcgagggg gtgattagag ggaggagaat gagcctcggc ctcttccgtg    2760
acgtcactgg accactgggc aatgatgcaa attttgtaac gaagacacag actgcgattt    2820
gtcccaggtc ctcactaccg ggcgcaggag ggtgagcgtt attggtcggc agccttctgg    2880
gcagaccttg acctcgtggg ctaggatgac taaaatattt attttttta agtatttagg      2940 ttttttgtttg tttcctttgt tcttacctgt atgtctccag tatccacttt gcacagctct   3000
ccggtctctc tctctctaca aactcccact tgtcatgtga caggtaaact atcttggtga    3060 atttttttt cctagccctc tcacatttat gaagcaagcc ccacttattc cccattcttc     3120
ctagtttcct cctcccagga actgggccaa ctcacctgag tcaccctacc tgtgcctgac    3180
cctacttctt ttgctcttag ctgtctgctc agacagaacc cctacatgaa acagaaacaa    3240
aaacactaaa aataaaaatg gccatttgct ttttcaccag atttgctaat ttatcctgaa    3300
atttcagatt cccagagcaa ataaatttta aacaaaggtt gagatgtaaa aggtattaaa    3360
ttgatgttgc tggactgtca tagaaattac acccaaagag gtatttatct ttacttttaa    3420
acagtgagcc tgaattttgt tgctgttttg atttgtactg aaaaatggta attgttgcta    3480
atcttcttat gcaatttcct ttttttgttat tattacttat ttttgacagt gttgaaaatg   3540
ttcagaaggt tgctctagat tgagagaaga gacaaacacc tcccaggaga cagttcaaga   3600
aagcttcaaa ctgcatgatt catgccaatt agcaattgac tgtcactgtt ccttgtcact    3660
ggtagaccaa aataaaacca gctctactgg tcttgtggaa ttgggagctt gggaatggat    3720
cctggaggat gcccaattag ggcctagcct taatcaggtc ctcagagaat ttctaccatt    3780
tcagagaggc cttttggaat gtggcccctg aacaagaatt ggaagctgcc ctgcccatgg    3840
gagctggtta aaatgcaga atcctaggct ccaccccatc cagttcatga gaatctatat     3900
ttaacaagat ctgcaggggg tgtgtctgct cagtaatttg aggacaacca ttccagactg    3960
cttccaattt tctggaatac atgaaatata gatcagttat aagtagcagg ccaagtcagg    4020
ccttattttc aagaaactga ggaatttttct ttgtgtagct ttgctctttg gtagaaaagg   4080
ctaggtacac agctctagac actgccacac agggtctgca aggtctttgg ttcagctaag    4140
ctaggaatga aatcctgctt cagtgtatgg aaataaatgt atcatagaaa tgtaactttt    4200
gtaagacaaa ggttttcctc ttctattttg taaactcaaa atatttgtac atagttattt    4260
atttattgga gataatctag aacacaggca aaatccttgc ttatgacatc acttgtacaa    4320
aataaacaaa taacaatgtg aaaaaaaaa aaaaaaaaa aaaaaaaa aaaaaaaaa         4380 ggtagcagtc gacagatgaa ttccaccaca ctggactagt ggatccgagc tcggtaccaa    4440
gcttaagttt aaac                                                      4454
```

<210> SEQ ID NO 5
<211> LENGTH: 649
<212> TYPE: DNA
<213> ORGANISM: Homo sapien
<220> FEATURE:
<221> NAME/KEY: misc_feature
<222> LOCATION: 335
<223> OTHER INFORMATION: n = A,T,C or G

<400> SEQUENCE: 5

```
tctagacgcg ttgacattga ttattgacta gttattaata gtaatcaatt acgggtcat      60
tagttcatag cccatgatat catatggagt tccgcgttac ataacttacg gtaaatggcc    120
cgcctggctg accgcccaac gacccccgcc cattgacgtc aataatgacg tatgttccca    180
tagtaacgcc aatagggact tccattgac gtcaatgggt ggagtattta cggtaaactg     240
cccacttggc agtacatcaa gtgtatcata tgccaagtac gccccctat tgacgtcaat     300
gacggtaaat ggcccgcctg gcattatgcc cagtncatga ccttatggga ctttcctact    360
tggcagacat ctacgtatta gtcatcgcta ttaccatggt gatgcggttt tggcagtaca    420
tcaatgggcg tggatagcgg tttgactcac ggggattttc caagtctcca ccccattgac    480
gtcaatggga gtttgttttg gcaccaaaat caacgggact ttccaaaatg tcgtaacaac    540
tccgccccat tgacgcaaat gggcggtagg cgtgtacggt gggaggtcta tataagcaga   600
gctctctggc taactagaga acccctgctt actggcttat cgagatatc                649
```

<210> SEQ ID NO 6
<211> LENGTH: 3693
<212> TYPE: DNA
<213> ORGANISM: Homo sapien

<400> SEQUENCE: 6

```
ggcagcgcgc agcggcaaga agtgtctggg ctgggacgga caggagaggc tgtcgccatc      60
ggcgtcctgt gcccctctgc tccggcacgg ccctgtcgca gtgcccgcgc tttccccggc    120
gcctgcacgg ggcgcgcctg ggtaacatgc ttggggtcct ggtccttggc gcgctggccc    180
tggccggcct ggggttcccc gcacccgcag agccgcagcc gggtggcagc cagtgcgtcg    240
agcacgactg cttcgcgctc tacccggggcc ccgcgacctt cctcaatgcc agtcagatct    300
gcgacggact gcggggccac ctaatgacag tgcgctcctc ggtggctgcc gatgtcattt    360
ccttgctact gaacgcgac ggcggcgttg ccgccggcg cctctggatc ggcctgcagc      420
tgccacccgg ctgcggcgac cccaagcgcc tcgggcccct gcgcggcttc cagtgggtta    480
cgggagacaa caacaccagc tatagcaggt gggcacggct cgacctcaat ggggctcccc    540
tctgcggccc gttgtgcgtc gctgtctccg ctgctgaggc cactgtgccc agcgagccga   600
tctgggagga gcagcagtgc gaagtgaagg ccgatggctt cctctgcgag ttccacttcc    660
cagccacctg caggccactg gctgtggagc ccggcgccgc ggctgccgcc gtctcgatca    720
cctacggcac cccgttcgcg gcccgcgag cggacttcca ggcgctgccg gtgggcagct    780
ccgccgcggt ggctcccctc ggcttacagc taatgtgcac cgcgccgccc ggagcggtcc    840
aggggcactg ggccagggag gcgccggggcg cttgggactg cagcgtggag aacggcggct    900
gcgagcacgc gtgcaatgcg atccctgggg ctccccgctg ccagtgccca gccggcgccg    960
ccctgcaggc agacgggcgc tcctgcaccg catccgcgac gcagtcctgc aacgacctct   1020
gcgagcactt ctgcgttccc aaccccgacc agccgggctc ctactcgtgc atgtgcgaga   1080
```

-continued

```
ccggctaccg gctggcggcc gaccaacacc ggtgcgagga cgtggatgac tgcatactgg    1140
agcccagtcc gtgtccgcag cgctgtgtca acacacaggg tggcttcgag tgccactgct    1200
accctaacta acgacctggt ggacggcgag tgtgtggagc ccgtggaccc gtgcttcaga    1260
gccaactgcg agtaccagtg ccagcccctg aaccaaacta gctacctctg cgtctgcgcc    1320
gagggcttcg cgcccattcc ccacgagccg cacaggtgcc agatgttttg caaccagact    1380
gcctgtccag ccgactgcga ccccaacacc caggctagct gtgagtgccc tgaaggctac    1440
atcctggacg acggtttcat ctgcacggac atcgacgagt gcgaaaacgg cggcttctgc    1500
tccggggtgt gccacaacct ccccggtacc ttcgagtgca tctgcgggcc cgactcggcc    1560
cttgcccgcc acattggcac cgactgtgac tccggcaagg tggacggtgg cgacagcggc    1620
tctggcgagc cccgcccag cccgacgccc ggctccacct tgactcctcc ggccgtgggg    1680
ctcgtgcatt cgggcttgct cataggcatc tccatcgcga gcctgtgcct ggtggtggcg    1740 cttttgcgc tcctctgcca cctgcgcaag aagcagggcg ccgccagggc caagatggag    1800
tacaagtgcg cggccccttc caaggaggta gtgctgcagc acgtgcggac cgagcggacg    1860
ccgcagagac tctgagcggc ctccgtccag gagcctggct ccgtccagga gcctgtgcct    1920
cctcacccca gctttgctac caaagcacct tagctggcat tacagctgga gaagaccctc    1980
cccgcacccc ccaagctgtt ttcttctatt ccatggctaa ctggcgaggg ggtgattaga    2040
gggaggagaa tgagcctcgg cctcttccgt gacgtcactg gaccactggg caatgatggc    2100
aattttgtaa cgaagacaca gactgcgatt tgtcccaggt cctcactacc gggcgcagga    2160
gggtgagcgt tattggtcgg cagccttctg ggcagacctt gacctcgtgg gctagggatg    2220
actaaaatat ttatttttt taagtattta ggttttgtt tgtttccttt gttcttacct    2280
gtatgtctcc agtatccact ttgcacagct ctccggtctc tctctctcta caaactccca    2340
cttgtcatgt gacaggtaaa ctatcttggt gaattttttt ttcctagccc tctcacattt    2400
atgaagcaag ccccacttat tccccattct tcctagtttt ctcctcccag gaactgggcc    2460
aactcacctg agtcacccta cctgtgcctg accctacttc ttttgctctt agctgtctgc    2520
tcagacagaa cccctacatg aaacagaaac aaaaacacta aaataaaaa tggccatttg    2580 ctttttcacc agatttgcta atttatcctg aaatttcaga ttcccagagc aaaataattt    2640
taaacaaagg ttgagatgta aaaggtatta aattgatgtt gctggactgt catagaaatt    2700
acacccaaag aggtatttat ctttacttt aaacagtgag cctgaatttt gttgctgttt    2760
tgatttgtac tgaaaaatgg taattgttgc taatcttctt atgcaatttc cttttttgtt    2820
attattactt attttgaca gtgttgaaaa tgttcagaag gttgctctag attgagagaa    2880
gagacaaaca cctcccagga gacagttcaa gaaagcttca aactgcatga ttcatgccaa    2940
ttagcaattg actgtcactg ttccttgtca ctggtagacc aaaataaaac cagctctact    3000
ggtcttgtgg aattgggagc ttgggaatgg atcctggagg atgcccaatt agggcctagc    3060
cttaatcagg tcctcagaga atttctacca tttcagagag gccttttgga atgtggcccc    3120
tgaacaagaa ttggaagctg ccctgcccat gggagctggt tagaaatgca gaatcctagg    3180
ctccacccca tccagttcat gagaatctat atttaacaag atctgcaggg ggtgtgtctg    3240
ctcagtaatt tgaggacaac cattccgac tgcttccaat tttctggaat acatgaaata    3300
tagatcagtt ataagtagca ggccaagtca ggcccttatt ttcaagaaac tgaggaattt    3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
```

```
tggaaataaa tgtatcatag aaatgtaact tttgtaagac aaaggttttc ctcctctatt    3540
ttgtaaactc aaaatatttg tacatagtta tttatttatt ggagataatc tagaacacag    3600
gcaaaatcct tgcttatgac atcacttgta caaaataaac aaataacaat gtgaaaaaaa    3660
aaaaaaaaaa aaaaaaaaa aaaaaaaaa aaa                                   3693
```